(12) United States Patent
Patricelli

(10) Patent No.: US 7,083,987 B2
(45) Date of Patent: Aug. 1, 2006

(54) ACTIVITY BASED PROBE ANALYSIS

(75) Inventor: Matthew P. Patricelli, San Diego, CA (US)

(73) Assignee: Activx Biosciences, Inc., La Jolla, CA (US)

( * ) Notice: Subject to any disclaimer, the term of this patent is extended or adjusted under 35 U.S.C. 154(b) by 185 days.

(21) Appl. No.: 10/049,164

(22) PCT Filed: Feb. 5, 2002

(86) PCT No.: PCT/US02/03808

§ 371 (c)(1),
(2), (4) Date: Oct. 21, 2002

(87) PCT Pub. No.: WO02/063271

PCT Pub. Date: Aug. 15, 2002

(65) Prior Publication Data

US 2003/0175986 A1      Sep. 18, 2003

Related U.S. Application Data

(60) Provisional application No. 60/339,424, filed on Dec. 11, 2001, provisional application No. 60/266,687, filed on Feb. 5, 2001.

(51) Int. Cl.
| | | |
|---|---|---|
| *G01N 33/533* | (2006.01) | |
| *G01N 21/76* | (2006.01) | |
| *C07K 1/13* | (2006.01) | |
| *C07H 19/167* | (2006.01) | |

(52) U.S. Cl. .................. 436/546; 436/86; 436/172; 436/800; 530/402; 536/26.1

(58) Field of Classification Search ............... 436/546, 436/86, 172, 800; 530/402; 536/26.1
See application file for complete search history.

(56) References Cited

U.S. PATENT DOCUMENTS

| | | | |
|---|---|---|---|
| 4,415,655 A | 11/1983 | de Castro et al. | |
| 4,433,051 A | 2/1984 | Gilad et al. | |
| 4,481,094 A | 11/1984 | Fernandez de Castro et al. | |
| 4,865,707 A | 9/1989 | Karger et al. | |
| 4,946,794 A | 8/1990 | Berube | |
| 4,978,614 A * | 12/1990 | Bronstein ................. | 435/21 |
| 5,728,529 A | 3/1998 | Metzker et al. | |
| 6,008,373 A | 12/1999 | Waggoner et al. | |
| 6,064,754 A | 5/2000 | Parekh et al. | |
| 6,087,101 A | 7/2000 | Gruelich et al. | |
| 6,127,134 A | 10/2000 | Minden et al. | |
| 6,130,101 A | 10/2000 | Mao et al. | |

FOREIGN PATENT DOCUMENTS

| | | |
|---|---|---|
| WO | WO 99/18921 | 4/1999 |
| WO | WO 00/00823 | 1/2000 |
| WO | WO 00/11208 | 3/2000 |
| WO | WO 00/36151 A1 | 6/2000 |
| WO | WO 01/77668 | 10/2001 |

OTHER PUBLICATIONS

Cravatt and Sorensen, "Chemical strategies for the global analysis of protein function", *Curr. Opin. Chem. Biol.* 4(6):663-8 (Dec. 2000).
Deutscher (ed.), *Methods in Enzymology* 182:147-238 (1990).
Gee et al., Fluorescent Bocillins: Synthesis and application in the detection of penicillin-binding proteins, *Electrophoresis* 2001, 22:960-965.
"Handbook of Fluorescent Probes and Research Products," Molecular Probes, Inc., 2001.
Kidd et al., "Profiling Serine Hydrolase Activities in Complex Proteomes," *Biochemistry* 40:4005-15 (2001).
Laemmli, UK, *Nature* 227:680-685 (1970).
Liu et al., Activity-based protein profiling: The serine hydrolases *Proc. Natl. Acad. Sci.* 96(26):14694 (1999).
Patricelli et al., "Direct Visualization of serine hydrolase activities in complex proteomes using fluorescent active site-directed probes," *Proteomics* 1:1067-71 (2001).
Scholze et al., "Fluorescent Inhibitors for the Qualitative and Quantitative Analysis of Lipolytic Enzymes," *Anal. Biochem.* 276:72-80.
Wang, G. and Geng. L., *Anal. Chem.* 72:4531-4542 (2000).

(Continued)

*Primary Examiner*—Long V. Le
*Assistant Examiner*—Shafiqul Haq
(74) *Attorney, Agent, or Firm*—Foley & Lardner LLP; Stephen E. Reiter

(57) ABSTRACT

Methods and compositions are described for analyzing complex protein mixtures using fluorescent activity-based probes. In particular, probes that specifically react with and bind to the active form of one or more target proteins are employed. Fluorescent signals obtained from the labeled active target proteins can be related to the presence or amount of active members of the desired target protein class. The methods and compositions described herein can be used, for example, to provide diagnostic information concerning pathogenic states, in identifying proteins that may act as therapeutic targets, and in drug discovery.

21 Claims, 1 Drawing Sheet

OTHER PUBLICATIONS

Zhao et al., "Bocillin FL, a Sensitive and Commercially Available Reagent for Detection of Penicillin-Binding Proteins," *Antim. Agents and Chem.* May 1999, 1124-1128.

Supplementary European Search Report for Application No. EP 02714857.6-2404-US0203808.

Urwin and Jackson, "A Multiple high-resolution mini two-dimensional polyacrylamide gel electrophoresis system: Imaging two-dimensional gels using a cooled charge-coupled device after staining with silver or labeling with fluorophore." Analytical Biochemistry 195:30-37, 1991.

Greenbaum et al., Expoxide electrophiles as activity-dependent cysteine protease profiling and discovery tools. Chemistry & Biology, 7:569-581, 2000.

Adam et al., Profiling the specific reactivity of the proteome with non-directed activity-based probes. Chemistry & Biology, 8:81-95, 2001.

Cravatt and Sorensen, Chemical strategies for the global analysis of protein function, Current Opinioin in Chemical Biology, 4:663-668, 2000.

Liu et al., Activity-based protein profiling: The serine hydrolases, PNAS, 96:14694-14699, 1999.

Patricelli et al., Direct visualization of serine hydrolase activities in complex proteomes using fluorescent active site-directed probes. Proteomics, 1:1067-1071, 2001.

Bogyo et al., Covalent modification of the active site threonine of proteasomal β subunits and the *Escherichia coli* homolog HsIV by a new class of inhibitors. PNAS, 94:6629-6634, 1997.

International Search Report for Application No. PCT/US02/03808.

* cited by examiner

ACTIVITY BASED PROBE ANALYSIS

This application claims priority to provisional U.S. patent application Ser. No. 60/266,687, filed Feb. 5, 2001; and to provisional U.S. patent application Ser. No. 60/339,424, filed Dec. 11, 2001, each of which is hereby incorporated by reference in its entirety, including all tables, figures, and claims.

FIELD OF THE INVENTION

The field of the invention is the analysis of proteomes.

BACKGROUND

The following discussion of the background of the invention is merely provided to aid the reader in understanding the invention and is not admitted to describe or constitute prior art to the present invention.

Determination of the genomic sequence of higher organisms, including humans, is now an attainable goal. However, this analysis represents only one aspect of the information encoded by the genome. Genes are expressed in an ordered and timely manner, and also exhibit a precise spatial and temporal expression pattern. Consequently, knowing the sequence of the genome is insufficient to explain biology and to understand disease.

More significantly, genes are transcribed to messenger RNA, which is then translated to protein. It is the protein, or gene product, that exhibits activity, and carries out the work of the cell. With the post-genome era rapidly approaching, new strategies for the analysis of proteins are being developed. Most conventional approaches focus on recording variations in protein level. These approaches are commonly referred to as "proteomics". In general, proteomics seeks to measure the abundance of broad profiles of proteins from complex biological mixtures.

In the most common embodiments, proteomics involves separating the proteins within a sample by two-dimensional electrophoresis. Then, the individual protein spot patterns of these gels can be compared to get indications as to the relative abundance of a particular protein in two comparative samples. The approach can even be extended to determine the molecular identity of the individual protein spots by excising the spots and subjecting them to peptide mass fingerprinting. For example, U.S. Pat. No. 6,064,754, which is hereby incorporated by reference in its entirety, including all figures, tables, and claims, describes computer-assisted methods for separating biomolecules and identifying biomolecule subsets by comparing profiles of the biomolecules obtained in gel electrophoretic separations.

More recently, methods have been described for eliminating the electrophoresis steps and performing proteomics by directly analyzing the complex mixture by mass spectrometry. For example, methods currently described in the art provide chemically reactive probes that can be reacted with a protein mixture to label many proteins in that mixture in a non-specific, or non-directed, manner providing a quantitative analysis only of protein abundance (see Aebersold, PCT/US99/19415). Such methods disclose that there are many chemically reactive amino acid residues within a protein which are individually reactive and which can be conjugated to chemical probes, whereby protein conjugates can be subsequently quantified to yield an indication of protein abundance Similarly, Wells et al. (PCT/US99/14267; PCT/US98/21759) disclose methods for identifying small organic molecule ligands that bind to biological target molecules without the requirement that the ligand bind to an active site on a target molecule. See also, WO 00/00823 and WO 00/11208.

Workers have also described methods for profiling classes of proteins based on protein activity using "activity-based probes" or "ABPs." In these methods, molecules with a binding moiety directed to the active site of a given protein class (e.g., serine proteases) and linked to a biotin tag are used to differentiate active members of the protein class in a proteome from inactive members. See, e.g., Liu et al., Proc. Nat'l. Acad. Sci. USA 96: 14694–14699 (1999); Cravatt and Sorensen, Curr. Opin. Chem. Biol. 4: 663–668 (2000); Patricelli et al., Proteomics 1: 1067–71 (2001). Each of these references is hereby incorporated in its entirety.

With regard to analysis or proteins using fluorescent labels, Scholze et al., Anal. Biochem. 276: 72–80 discloses fluorescent inhibitors for analysis of lipases; U.S. Pat. No. 4,433,051 discloses an enzyme-activated irreversable inhibitor of omithine decarboxylase linked to a rhodamine moiety for use in cytochemical staining procedures. U.S. Pat. No. 6,127,134, which is hereby incorporated by reference in its entirety, including all figures, tables, and claims, discloses the analysis of protein mixtures using fluorescent compounds and separation using electrophoresis.

In determining active proteins in a complex protein mixture, the goal is typically to compare different assay compositions, so that one can relate the different compositions for better understanding of the nature of the protein mixture. There remains a need in the art for methods and compositions that permit different compositions to be accurately compared as to the presence and/or abundance of each of the different active proteins in the mixture.

SUMMARY OF THE INVENTION

The present invention describes compositions and methods for the design, synthesis, and use of fluorescent activity based probes ("fABPs") for the analysis of one or more active protein components of proteomes. As described herein, the fABPs of the present invention comprise a "warhead" (defined hereinafter) directed to a desired protein class covalently linked to a fluorescent moiety. By carefully selecting the design criteria of the fABP, e.g., using a combinatorial library approach, a structure-based design approach, or a combination of approaches, fABPs can be synthesized that provide a sensitive and specific signal that can be related to the presence or amount of active members of the desired protein class.

Thus, in a first aspect, one or more complex protein mixtures are analyzed for active protein components using fABPs. In these embodiments, fABPs are contacted with a complex protein mixture, preferably a proteome, under conditions in which the fABPs react with, and thereby label, active target proteins. The labeled target proteins may then be selectively detected and/or isolated in order to determine the presence or amount of one or more active proteins in the complex mixture. The detected and/or isolated proteins are characteristic of the presence of a protein function, e.g., an enzymatic activity, protein complex formation, protein-nucleic acid interactions, etc., in the analyzed mixture.

In various preferred embodiments, the labeled target proteins in two or more complex protein mixtures, preferably two or more proteomes, may be compared to one another. In certain embodiments, this comparison may comprise comparing a native mixture and an inactivated mixture that have been treated with the fABPs, where the fABPs may be multiplexed to bond to different types of proteins. The mixtures are then separated, and common fluorescent bands from the two samples may be ignored, while the fluorescent bands that differ in signal between the native and inactive mixtures indicate active protein.

Alternatively, this comparison may comprise comparing a complex protein mixture obtained from normal tissue(s) to a complex protein mixture obtained from diseased tissue(s). The mixtures are then separated, and fluorescent bands from the two samples may be analyzed for relative signal intensity. Bands that are different in the two mixtures may indicate markers associated with normal or diseased states.

In yet another alternative, this comparison may comprise comparing a complex protein mixture obtained from cell(s), tissue(s), or organism(s) treated with one or more compounds (e.g., lead compounds in drug discovery) to a complex protein mixture obtained from cell(s), tissue(s), or organism(s) not so treated. The mixtures may then be separated, and the pattern and/or relative intensities of fluorescent species in the samples may be compared. For example, common fluorescent bands from the two samples may be analyzed for relative signal intensity, while bands that are present in one sample, but absent in the other may be identified. Such methods may indicate alterations in active protein content due to the treatment regimen. Additionally, such methods can also differentiate between treatments that act by direct inhibition of specific proteins ("primary effects") versus treatments that affect active protein content upstream, e.g., by altering expression of protein (s). ("secondary effects")

In particularly preferred embodiments, gel electrophoresis is used for separation of the labeled complex protein mixture(s). Using gel electrophoresis permits rapid measurement providing for enhanced accuracy in a convenient protocol.

In various additional aspects, the instant invention relates in part to compositions and methods for analyzing complex proteomes, using fABPs. In other aspects, the present invention also relates in part to kits for performing proteome analysis using fABPs. Such kits may include one or more reagents required for contacting one or more proteomes with one or more fABPs, and may further include a protocol, separation reagents (e.g., electrophoresis gels and buffers), etc. In yet other aspects, the instant invention relates in part to devices configured to perform proteome analysis using the compositions and methods described herein.

In yet other aspects, the present invention also relates to methods for the design and synthesis of fABPs and libraries thereof. In various aspects, one or more of the following steps may be selected in order to obtain fABPs exhibiting advantageous sensitivity and specificity in proteomic assays: (i) a conserved (at the sequence level) reactive amino acid in a target site of the desired protein class is identified; (ii) a conserved (at the 3-dimensional structure level) reactive amino acid in a target site of the desired protein class is identified; (iii) solvent and/or steric availability of the reactive amino acid is assessed; (iv) one or more "warheads" comprising a desired functional group and, optionally, a desired affinity moiety are obtained; (v) one or more fluorescent moieties exhibiting desired properties are obtained; (vi) one or more linker moieties exhibiting desired properties are selected to join warheads to fluorescent moieties; (vii) a library of fABPs are obtained from the selected warhead(s), fluorescent moiet(ies), and linker moiety(ies); and (viii) the labeling profiles of the fABPs within the library are evaluated with regard to their proteome labeling profile.

DESCRIPTION OF THE PREFERRED EMBODIMENTS

Figure 1:
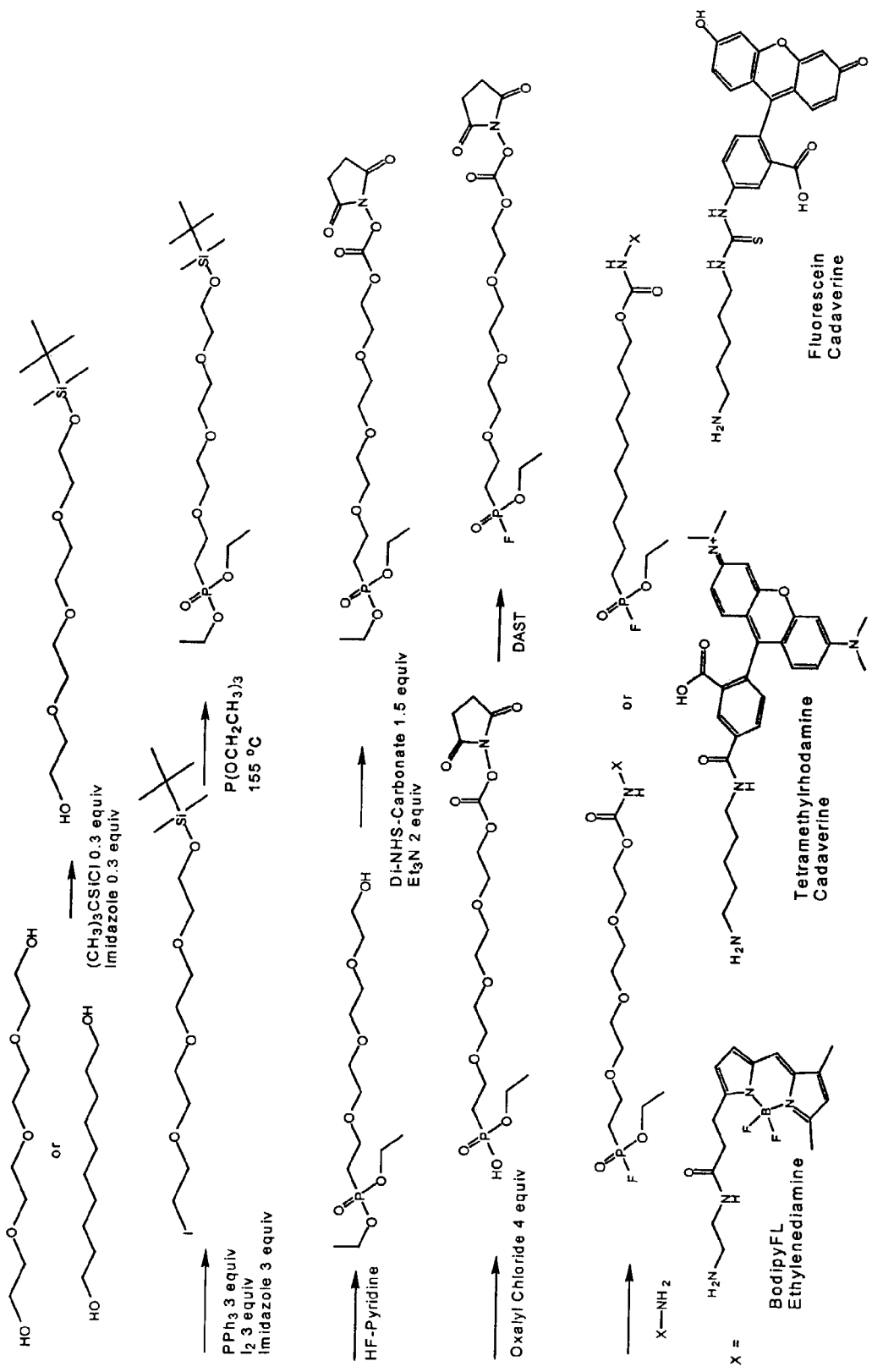
FIG. 1 is a flowchart of the synthesis of the fluorescent activity based probes with fluorophosphonates as the reactive group ("fABPs").

Methods and compositions are described for assaying complex protein mixtures for active target proteins. The methods and compositions described herein relate in part to fluorescent activity based probes ("fABPs") that preferentially react with active proteins as compared to inactive proteins and/or are members of a combinatorial library of probes from which useful probes are to be determined. The fABPs of the present invention can provide a number of advantageous characteristics when applied to proteomic analysis. These can include advantageous sensitivities combined with low background signals; reduced photolysis of the fABP molecules; and improved ability to capture labeled target proteins.

In preferred embodiments, the methods described herein involve adding one or a mixture of the fABPs to a plurality of different samples. For example, a first (e.g., a native) complex protein mixture under conditions where the primary reaction is with active proteins, and to a second complex protein mixture (e.g., one in which the proteins have been inactivated and/or to a native complex protein mixture from a source related to the source of the first test mixture). In cases where a plurality of fABPS have been added, each fABP species may have the same or different fluorescent moieties having the same and/or different absorption and emission spectra. In these embodiments, a single complex protein mixture may act as a reference, to which one or more test complex protein mixture(s) are compared (e.g., the effect of a number of compounds may each be assessed by comparing a number of treated samples to an individual untreated sample). Alternatively, all members of a plurality of complex protein mixtures may be compared to each other member of the plurality.

When using a probe combinatorial library, the members of the library can be selected to comprise different fluorescent moieties, different linker moieties, different points of connection between linker moiety and warhead and/or fluorescent moiety, and/or other indicia to be identified.

After sufficient time for reaction to occur, the labeled mixtures are analyzed, preferably by electrophoresis, most preferably by gel electrophoresis or capillary electrophoresis under denaturing or native conditions. In various embodiments, the samples may be combined in a single lane or analyzed in separate lanes in proximity to each other. Only those proteins with which the fABPs have reacted will be observed. The results from an inactivated sample may be subtracted from the results from a corresponding native sample to indicate those proteins that are active in the sample. In the case of the library, the positive conjugates may be further analyzed to determine the composition of the probe.

The subject fABPs find use for the most part with biological samples, which may have been subject to processing before reaction with the fABPs. "Biological sample" intends a sample obtained from a cell, tissue, or organism. Examples of biological samples include proteins obtained from cells (e.g., mammalian cells, bacterial cells, cultured cells), particularly as a lysate, a biological fluid, such as blood, plasma, serum, urine, bile, saliva, tears, cerebrospinal fluid, aqueous or vitreous humor, or any bodily secretion), a transudate or exudate (e.g. fluid obtained from an abscess or other site of infection or inflammation), a fluid obtained from a joint (e.g. a normal joint or a joint affected by disease such as rheumatoid arthritis, osteoarthritis, gout or septic arthritis), or the like.

Biological samples may be obtained from any organ or tissue (including a biopsy or autopsy specimen) or may comprise cells (including primary cells, passaged or cultured primary cells, cell lines, cells conditioned by a specific medium) or medium conditioned by cells. In preferred embodiments, a biological sample is free of intact cells. If desired, the biological sample may be subjected to prior processing, such as lysis, extraction, subcellular fractionation, and the like. See, Deutscher (ed.), 1990, Methods in Enzymology, vol. 182, pp. 147–238.

Of particular interest are samples that are "complex protein mixtures." As used herein, this phrase refers to protein mixtures having at least about 20, more usually at least about 50, even 100 or more different proteins, where the particular distribution of proteins is of interest. An example of such a complex protein mixture is a proteome, as defined hereinafter. Complex protein mixtures may be obtained from cells that are normal or abnormal in some particular, where the abnormality is informative as to treatment, status, disease, or the like, can be analyzed using the methods of the subject invention.

The subject method can be used for a variety of purposes. The method can be used in the diagnosis of disease, the response of cells to an external agent, e.g. a drug, staging diseases, such as neoplasia, identifying cell differentiation and maturation, identifying new proteins, screening for active drugs, determining side effects of drugs, identifying allelic response, identifying useful probes from combinatorial libraries, etc.

The system uses fABPs specific for the active form of a protein or a defined group of proteins, usually directed to an active site on such proteins, and combines one or a mixture of probes, depending on the specificity of the probes and the variety in the group or groups of related proteins to be assayed. In the present invention, it is not necessary that there be no reaction of an fABP with inactive target protein (s). Rather, an fABP is defined as being "specific for," as "specifically reacting with," or as "specifically binding to," active target protein(s) if the fABP provides at least about twice the amount of signal from fABP labeling of active protein when compared to an equivalent amount of inactive target protein. Preferably the signal obtained from active target protein(s) will be at least about five fold, preferably 10 fold, more preferably 25-fold, even more preferably 50-fold, and most preferably 100-fold or more, greater than that obtained from an equivalent amount of inactive target protein.

The term "target protein" as used herein refers to one or more proteins, an active site of which becomes labeled by one or more fABPs when the target protein is in its "active" form. The reaction mixture can provide conditions under which the fABP(s) react substantially preferentially with active target proteins. Particularly preferred target proteins are enzymes; other preferred target proteins include receptors, transcription factors, G-proteins, and the like.

The term "active target protein" refers to a protein that is in its native conformation and is able to interact with an entity with which it normally interacts, e.g. enzyme with substrate and cofactor, receptor with ligand, etc., e.g. phosphorylated active form as compared to unphosphorylated inactive form and vice versa. In effect, the protein is in the form in which it can carry out its biological function.

The term "inactivated" as used herein refers to a sample that has been treated so that at least a portion of target proteins that were active in the original sample are rendered inactive. An "inactive protein" can result from various mechanisms such as denaturation, inhibitor binding, either covalently or non-covalently, mutation, secondary processing, e.g. phosphorylation or dephosphorylation, etc. Functional states of proteins or enzymes as described herein may be distinct from the level of abundance of the same proteins or enzymes.

The term "untreated" as used herein refers to a sample that has not been exposed to one or more conditions as compared to a second, otherwise identical sample. An untreated sample may be a sample that has not been inactivated; alternatively, an untreated sample may be one not exposed to one or more molecules (e.g., drug lead compounds) in a screening assay.

An "active site" of a protein refers to the specific area on the surface of a protein, e.g., an enzyme molecule or surface membrane receptor, to which a binding molecule, e.g. substrate or reciprocal ligand, is bound and results in a change in the ligand and/or protein, e.g. substrate or complex formation with the protein as a result of ligand binding. For a receptor, the conformation may change, the protein may become susceptible to phosphorylation or dephosphorylation or other processing. For the most part, the active site will be the site(s) of an enzyme where the substrate and/or a cofactor bind, where the substrate and cofactor undergo a catalytic reaction; where two proteins form a complex, e.g. the site at which a G protein binds to a surface membrane receptor, two kringle structures bind, sites at which transcription factors bind to other proteins; or sites at which proteins bind to specific nucleic acid sequences, etc.

The subject methods employ fABPs that react with active target proteins and allow for the selective detection and subsequent isolation of active proteins from complex mixtures. The isolated proteins are characteristic of the presence of a protein function, e.g., an enzymatic activity, protein complex formation, protein-nucleic acid interactions, etc., in those mixtures. Using the fABPs of the present invention, labeled active target proteins may be identified by excitation and detection of light emitted upon excitation of the fluorescent moiety, e.g., in electrophoresis gels.

In certain embodiments, such as when the fABP labels a plurality of active target proteins or when the identity of a labeled active target protein is unknown, the labeled active target proteins present in various electophoretic bands may be further assayed to identify the specific proteins to which the fABP(s) bound, e.g. by fragmentation and mass spectrometric analysis. In particular, the sequence of proteins can be determined using tandem MS ($MS^n$) techniques. By application of sequence database searching techniques, the protein from which a sequenced peptide originated can be identified.

In referring to affinity for an fABP to an active target protein, one is concerned with the on-rate of the fABP with the active target protein, since there is a negligible off-rate, where the fABP covalently bonds to the active target protein. One can determine relative on-rates between fABPs by having less than a stoichiometric amount of the active target protein as compared to the total amount of one or more fABPs, and then measuring the relative amounts of the conjugates for each of the fABPs. In this way one can obtain a measure of the relative labeling rate of each of the fABPs toward the active target protein, which for the purposes of this invention may be considered the affinity, if not the binding affinity, of the fABP for the active target protein.

Exemplary target proteins include enzymes, such as oxidoreductases, hydrolases, ligases, isomerases, transferases, and lyases (and including such enzymes or enzyme groups as serine hydrolases, metallo-hydrolases, dehydrogenases, e.g. alcohol and aldehyde dehydrogenases, and nucleotide triphosphate (NT)-dependent enzymes), although, the invention envisions fABPs which recognize any protein, e.g., enzyme, family. Other target proteins include proteins that bind to each other or to nucleic acids, such as transcription factors, kringle structure containing proteins, nucleic acid binding proteins, G-protein binding receptors, cAMP binding proteins, etc.

Structure of fABPs

The fABPs of the present invention comprise a warhead, linked via a linker moiety ("L") to a fluorescent moiety ("F1"). As will be described hereinafter, each of the warhead, the linker moiety, and the fluorescent moiety may be independently selected to provide different target specificities. Each of these components of an fABP is described in additional detail below.

The term "warhead" as used herein refers to the portion of an fABP that is directed to and binds with an active site of an active target protein. The warhead comprises a functional group ("F") and an optional affinity moiety ("R"). Functional group (F) refers to one or more chemical groups within an fABP that specifically and covalently bond to the active site of a protein. The functional group may, by its very structure, be directed to the active site of a target protein. Alternatively, a separate affinity moiety (R) may be provided. Affinity moiety (R) refers to a chemical group, which may be a single atom, that is conjugated to the functional group or associated with the linker moiety that provides enhanced binding affinity for protein targets and/or changes the binding profile of the warhead. The affinity moiety is preferably less than 1 kilodalton in mass.

The term "linker moiety" refers to a bond or chain of atoms used to link one moiety to another, serving as a covalent linkage between two or more moieties.

The term "fluorescent moiety" refers to a portion of an fABP that can be excited by electromagnetic radiation, and that emits electromagnetic radiation in response in an amount sufficient to be detected in an assay. The skilled artisan will understand that a fluorescent moiety absorbs and emits over a number of wavelengths, referred to as an "absorbance spectrum" and an "emission spectrum." A fluorescent moiety will exhibit a peak emission wavelength that is a longer wavelength than its peak absorbance wavelength. The term "peak" refers to the highest point in the absorbance or emission spectrum.

The fABP will have an affinity for an active site, which may be specific for a particular active site or generally shared by a plurality of related proteins. The affinity may be affected by the choice of the functional group, the linker moiety, the binding moiety, the fluorescent moiety, or a combination thereof. As described hereinafter, one or more fABPs may be designed that exhibit specificity for a single target protein, or that exhibit specificity for a plurality of targets that may be structurally or functionally related.

The fABPs of the subject invention may be illustrated by the following formula:

where * indicates that R may be optionally present, and L, if present, may be bound to either F, L or both F and L.

Exemplary Fs as used in an fABP of the invention include an alkylating agent, acylating agent, ketone, aldehyde, sulphonate or a phosphorylating agent. Examples of particular Fs include, but are not limited to fluorophosphonyl, fluorophosphoryl, fluorosulfonyl, alpha-haloketones or aldehydes or their ketals or acetals, respectively, alpha-haloacyls, nitriles, sulfonated alkyl or aryl thiols, iodoacetylamide group, maleimides, sulfonyl halides and esters, isocyanates, isothiocyanantes, tetrafluorophenyl esters, N-hydroxysuccinimidyl esters, acid halides, acid anhydrides, unsaturated carbonyls, alkynes, hydroxamates, alpha-halomethylhydroxamates, aziridines, epoxides, or arsenates and their oxides. Sulfonyl groups may include sulfonates, sulfates, sulfinates, sulfamates, etc., in effect, any reactive functionality having a sulfur group bonded to two oxygen atoms. Epoxides may include aliphatic, aralkyl, cycloaliphatic and spiro epoxides, the latter exemplified by fumagillin, which is specific for metalloproteases.

The linker moiety L, which potentially can be as short as a covalent bond, is preferred to be other than a bond. Since in many cases, the synthetic strategy will be able to include a functionalized site for linking, the functionality can be taken advantage of in choosing the linking moiety. The choice of linker moiety has been shown to alter the specificity of an ABP. See, e.g., Kidd et al., *Biochemistry* (2001) 40: 4005–15. For example, an alkylene linker moiety and a linker moiety comprising a repeating alkyleneoxy structure (polyethylene glycols, or "PEG"), have distinct specificities and provide distinct protein profiles. Thus, one of skill in the art can select the linker moiety of the fABP in order to provide additional specificity of the fABP for a particular protein or protein class.

Linker moieties include among others, ethers, polyethers, diamines, ether diamines, polyether diamines, amides, polyamides, polythioethers, disulfides, silyl ethers, alkyl or alkenyl chains (straight chain or branched and portions of which may be cyclic) aryl, diaryl or alkyl-aryl groups, having from 0 to 3 sites of aliphatic unsaturation. While normally amino acids and oligopeptides are not preferred, when used they will normally employ amino acids of from 2–3 carbon atoms, i.e. glycine and alanine. Aryl groups in linker moieties can contain one or more heteroatoms (e.g., N, O or S atoms). The linker moieties, when other than a bond, will have from about 1 to 60 atoms, usually 1 to 30 atoms, where the atoms include C, N, O, S, P, etc., particularly C, N and O, and will generally have from about 1 to 12 carbon atoms and from about 0 to 8, usually 0 to 6 heteroatoms. The number of atoms referred to above are exclusive of hydrogen in referring to the number of atoms in a group, unless indicated otherwise.

Linker moieties may be varied widely depending on their function, including alkyleneoxy and polyalkyleneoxy groups, where alkylene is of from 2–3 carbon atoms, methylene and polymethylene, polyamide, polyester, and the like, where individual monomers will generally be of from 1 to 6, more usually 1 to 4 carbon atoms. The oligomers will generally have from about 1 to 10, more usually 1 to 8 monomeric units. The monomeric units may be amino acids, both naturally occurring and synthetic, oligonucleotides, both naturally occurring and synthetic, condensation polymer monomeric units and combinations thereof.

The fluorescent moiety may be varied widely depending upon the protocol to be used, the number of different probes employed in the same assay, whether a single or plurality of lanes are used in the electrophoresis, the availability of excitation and detection devices, and the like. For the most part, the fluorescent moieties that are employed will absorb in the ultraviolet, infrared, and/or most preferably in the visible range and emit in the ultraviolet, infrared, and/or most preferably in the visible range. Absorption will generally be in the range of about 250 to 750 nm and emission will generally be in the range of about 350 to 800 nm. Illustrative fluorescent moieties include xanthene dyes, naphthylamine dyes, coumarins, cyanine dyes and metal chelate dyes, such as fluorescein, rhodamine, rosamine, the BODIPY dyes (FL, TMR, and TR), dansyl, lanthamide cryptates, erbium, terbium and ruthenium chelates, e.g. squarates, and the like. Additionally, in certain embodiments, one or more fluorescent moieties can be energy transfer dyes such as those described in Waggoner et al., U.S. Pat. No. 6,008,373. The literature amply describes methods for linking fluorescent moieties through a wide variety of linker moieties to other groups. The fluorescent moieties that find use will normally be under 2 kDal, usually under 1 kDal.

Preferred fluorescent moieties can include elaborated conjugated pyran molecules, including xanthenes. Such molecules include eosin, erythrosin, fluorescein, Oregon green, and various commercially available Alexa Fluor® dyes (Molecular Probes, Inc.). Structural examples of such dyes include:

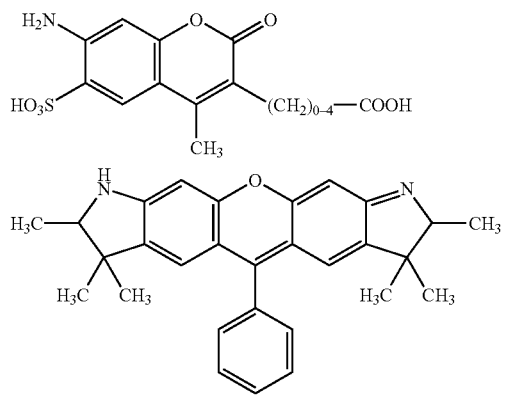

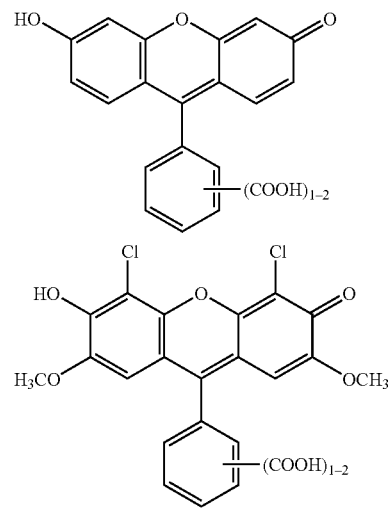

Particularly preferred fluorescent moieties are the rhodamine dyes. These molecules typically have the general structure:

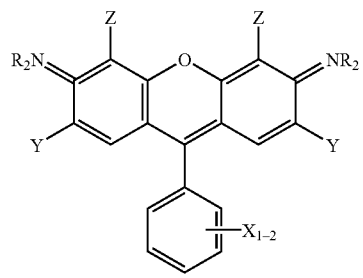

Where X is —$CO_2H$, or —$SO_3H$; Y is —H, —$CH_3$, or together with R forms a six-membered ring; Z is —H or together with R forms a six-membered ring; and R is —H, —$CH_3$, —$CH_2CH_3$, or together with Y or Z forms a six-membered ring. Rhodamine molecules such as tetramethylrhodamine, 5-carboxytetramethylrhodamine, 6-carboxytetramethylrhodamine, carboxyrhodamine-6G, rhodamine-B sulfonyl chloride, rhodamine-red-X, and carboxy-X-rhodamine are well known to those of skill in the art. See, e.g., Handbook of Fluorescent Probes and Research Products, Molecular Probes, Inc., 2001, which is hereby incorporated by reference in its entirety. Advantageous properties of rhodamines include high quantum yields, low sensitivity of fluorescence over a pH range of from about pH 3 to about pH 8, advantageous water solubility, good photostability, and absorption of light in the visible spectrum. Particularly preferred fluorescers are 5-carboxytetramethylrhodamine and 6-carboxytetramethylrhodamine.

Other preferred fluorescent moieties include the BODIPY dyes, which are elaborations of a 4-bora-3a,4a-diaza-s-indacene structure. Exemplary structures are provided below:

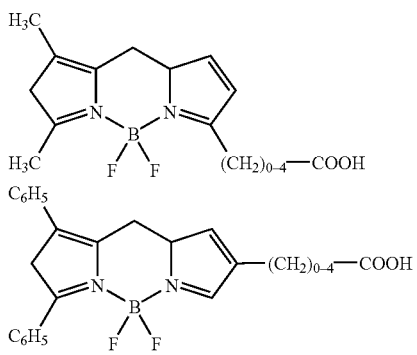

Yet other preferred fluorescent moieties include the cyanine dyes, conjugated structures comprising a polymethine chain terminating in nitrogen atoms. Typically, the nitrogens are themselves part of a conjugated heterocycle. An exemplary structures is provided below:

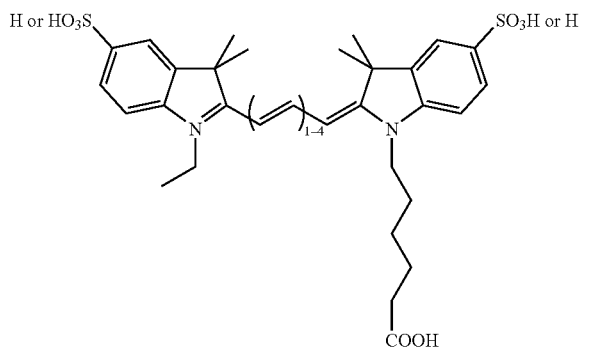

Also of interest is the use of matched dyes as described in U.S. Pat. No. 6,127,134, which is hereby incorporated by reference in its entirety, including all tables, figures, and claims, which is concerned with labeling proteins with dyes that have different emissions, but have little or no effect on relative migration of labeled proteins in an electrophoretic separation. Of particular interest are the cyanine dyes disclosed therein, being selected in '134 because of their positive charge, which matches the lysine to which the cyanine dyes bind. In addition there is the opportunity to vary the polyene spacer between cyclic ends, while keeping the molecular weight about the same with the introduction of an alkyl group in the shorter polyene chain dye to offset the longer polyene. Also described are the BODIPY dyes, which lack a charge. The advantage of having two dyes that similarly affect the migration of the protein would be present when comparing the native and inactived samples, although this would require that in the inactivated sample at least a portion of the protein is monosubstituted.

By "little or no effect on relative migration" is meant that, when proteins are labeled by different fABPs, the fABP has either substantially no effect on migration of each protein, or the fABP affects the migration of each protein by substantially the same amount. By "substantially no effect" is meant that a labeled protein migrates in a separation method within 10% of the rate of the unlabeled protein. By "substantially the same amount" means that the effect of fABPs on migration of each labeled protein is within 10% of the effect on each other labeled protein.

In each of the foregoing examples of preferred fluorescent moieties, carboxyl groups can provide convenient attachment sites for linker moieties. In the particularly preferred 5- and 6-carboxyrhodamine molecules, the 5- or 6-carboxyl is particularly preferred as an attachment site:

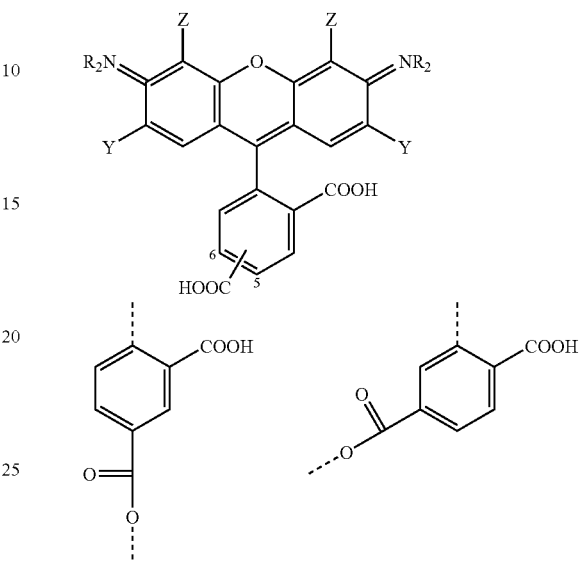

As discussed above, a number of functional groups can be used for the fABPs, such as an alkylating functionality, an acylating functionality, a ketone functionality, an epoxide functionality, praticularly a spiroexpoxide, olefins, an aldehyde functionality, a sulphonyl functionality and a phosphoryl functionality. Specificity can be achieved by having groups as part of the active functionality, e.g. sulfonate or sulfate esters, fluorophosphonates, substituted spiroepoxides, etc., where the substituents may be aliphatic, alicyclic, aromatic or heterocyclic or combinations thereof, aliphatically saturated or unsaturated, usually having fewer than 3 sites of unsaturation. Illustrative groups include as alkyl, heterocyclic, such as pyridyl, substituted pyridyl, imidazole, pyrrole, thiophene, furan, azole, oxazole, aziridine, etc., aryl, substituted aryl, amino acid or peptidyl, oligonucleotide or carbohydrate group. Many of the functionalities are found in the literature, such as fluorophosphonates, spiroepoxides, sulfonates, olefins, carbonyls, and the like. See, e.g., Cravatt B F & Sorensen E J, "Chemical strategies for the global analysis of protein function", Curr Opin Chem Biol 2000 December;4(6):663–8.

In some instances, it may be desirable to have a ligand associated with the fABP to allow all of the fABPs, whether conjugated to active target proteins or unconjugated, to be captured and washed free of other components of the reaction mixture. This can be of particular interest where, following capture, the protein bound to the fABP is partially degraded, leaving oligopeptides that are specific for the protein and can be analyzed with a mass spectrometer. Also, the ligand allows for a cleaner sample to be used for electrophoretic separation, by capture, wash and release. The ligand will generally be under about 1 kDal. Biotin is a conventional ligand, particularly analogs such as dethiobiotin and deiminobiotin, which can be readily displaced from strept/avidin by biotin. However, any small molecule will suffice that can be captured and released under convenient conditions.

In particularly preferred embodiments, the fluorescent moiety (e.g., a rhodamine such as 5- or 6-tetramethylrhodamine) of an fABP can act as this ligand. In these embodiments, an antibody may be selected that binds to the fluorescent moiety at an epitope such that binding of the antibody is not affected by fABP binding to its active target protein. For example, in the case of tetramethylrhodamine linked to a warhead through the pendant phenyl, antibodies may be selected that exhibit binding to the xanthene portion of the molecule. Such antibodies would both avoid steric incompatibilities, and advantageously be insensitive to the attachment point of the linker (e.g., the 5- or 6-carbon of the pendant phenyl). Exemplary methods for identifying suitable receptors (e.g., an antibody or a fragment thereof) for capture of antibody ligands are described hereinafter.

Design of fABPs and Libraries of fABPs fABPs of the invention may be designed and synthesized using combinatorial chemistry and/or rational design methods. Goals of a design strategy are to provide fABPs that are able to react covalently with a targeted group of active proteins, while minimizing non-specific labeling. While described below as a series of exemplary steps, the skilled artisan will understand that one or more of these steps may be eliminated, duplicated, or moved within the design sequence, according to the requirements of a given design strategy.

One strategy that may be utilized to design fABPs is to first identify a potentially reactive amino acid that is conserved at the sequence level in the region that is targeted for fABP labeling. Potential reactive amino acids include serine, threonine, tyrosine, lysine, arginine, aspartic acid, glutamic acid, asparagine, glutamine, methionine, and cysteine. For example, to design one or more kinase-directed fABPs, the ATP binding site represents an appropriate target site. A sequence search of 390 protein kinases reveals a lysine residue that is conserved in all but one of these kinase, as shown in the representative table below.

```
                    Lys⁷⁴⁵ in EGFR
                         ↓
EGFR      ... V A I K E L R E A T ...
INSR      ... V A V K T V N E S A ...
PDGFRa    ... V A V K M L K S T A ...
FGFR1     ... V A V K M L K S D A ...
SRC       ... V A I K T L K P G T ...
cAb1      ... V A V K T L K E D T ...
FAK       ... V A I K T C K N C T ...
cRaf      ... V A V K I L K V V D ...
PKCa      ... Y A I K I L K K D V ...
RhoK      ... Y A C K K L N K K R ...
Cdk2      ... V A L K K I R L D T ...
ERR1      ... V A I K K I S P F E ...
```

One can also determine whether the selected amino acid is structurally conserved. For example, atomic structural coordinates of representative proteins may be analyzed (either generated internally or when possible accessed via the publicly available Protein Data Bank (PDB)). Several criteria may be considered as indicating a useful reactive amino acid: the amino acid is (1) present in a region that is targeted for fABP labeling, (2) the amino acid is available for reactions with the fABP functional group and not buried within the protein, and (3) the amino acid is in the same general area in a large percentage of the protein family. For example, comparing a number of kinase crystal structures available from the PDB, indicates that the lysine residue identified above based upon sequence homology is also structurally conserved and meets the three criteria.

Additional information may also be obtained from the atomic structural coordinates concerning those parts of a protein that may be open to the solvent. This information can be used to identify where linker moieties can be attached to the warhead. It is desirable that the fluorescent moieties do not perturb binding interactions between the warhead and the protein. This is assured by positioning the fluorescent moiety so that it remains in the solvent and is not required to interact with the protein. For instance, when ATP is the bound to the kinases discussed above, it is readily observed that the 2' and 3'-hydroxyls point outward towards the solvent and away from the protein.

At this point fABPs may be constructed to interact with the protein binding region, have a functional group positioned in the vicinity of the targeted amino acid and possessing the correct reactivity to form a covalent bond with the targeted amino acid, and have the fluorescent moiety positioned in such a way that it will point out towards solvent and away from the protein binding region.

One can also consider the composition of the linker moiety between the warhead moiety and the fluorescent moiety of the fABP, as this can affect the selectivity and specificity of the resulting fABPs. As discussed above, linkers may be either obtained commercially (see, e.g., Pierce Chemical Company Catalog and Handbook 1994–95, pages O-90 through O-110, which is hereby incorporated by reference) or synthesized as needed. A library of molecules comprising, for example, linker chemistries exhibiting varying lengths, hydrophobicities, etc., may be constructed:

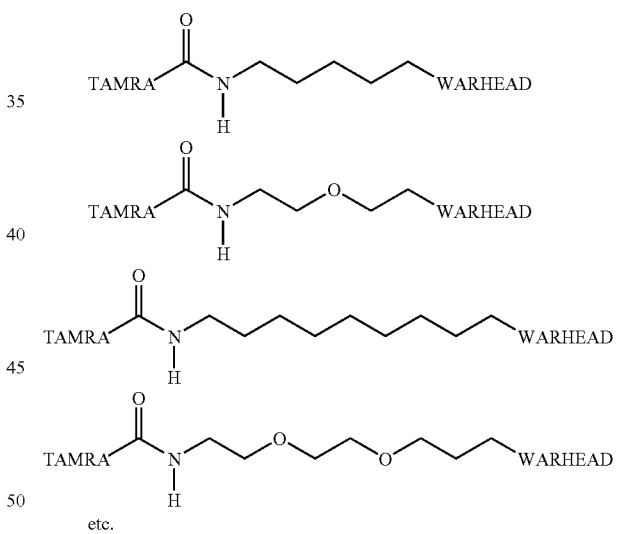

etc.

Moreover, the library of fABPs can also be expanded by varying identity of the fluorescent moiety, and/or the location of linker moiety attachment point on the fluorescent moiety (e.g., 5-TMR linkage vs. 6-TMR linkage), as these can also affect the selectivity and specificity of the resulting fABPs.

A typical library of fABPs may be designed, for example, to analyze protein compositions for groups of ATP dependent proteins, using affinity based probes specific for ATP binding sites in their natural conformation. Suitable affinity based probes might have an adenosine group as an affinity moiety, a functional group for reacting with the target protein and a fluorescent moiety that allows for identification, isolation or the like.

Such a library may consist of compounds in which the warhead comprises a functional group F attached to an affinity moiety R that is an analogue of adenosine, within the following formulae:

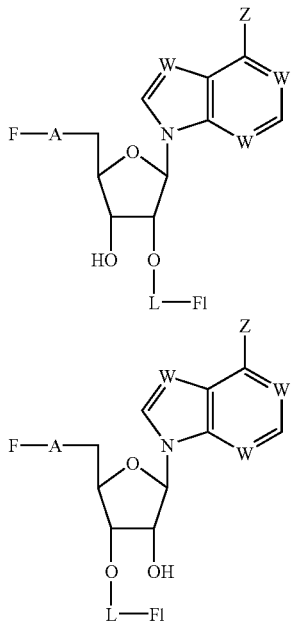

wherein
  each W is carbon or nitrogen, particularly nitrogen;
  Z is hydrogen or amino, particularly amino;
  F is a functional group capable of reacting with at least one of thiol, hydroxyl or amino joined through A to the 5' carbon of the ribose, where the functional group may be directly bonded to A or through a link of from about 2 to 12, usually not more than 10, more usually not more than about 8 carbon atoms and having from 0 to 4, usually 0 to 2 heteroatoms, including O, S, N and P, where the linkage may be aliphatic, alicyclic, aromatic or heterocyclic, the functional group being a single moiety or a combination of moieties comprising halogen, O, S, N, P, and C, where the groups may be fluorosulfonyl, fluorophosphonyl ester, halogen, epoxide or ethylene α to an activating group, such as sulfonyl, carbonyl, phosphonyl, phosphityl, etc., or halogen β to an activating group, such as amino, thio, etc.;
  A is NR, O, S or CH$_2$, wherein R is H or alkyl of from 1 to 6, usually 1 to 3 carbon atoms;
  Fl is a fluorescent moiety joined to the oxygen of the 2' and/or 3' position of the ribose through a linker moiety L of at least 2 atoms, that are carbon, oxygen, nitrogen and sulfur,
  where the entire molecule will generally have not more than about 75 carbon atoms and at least about 15 carbon atoms, usually at least about 20 carbon atoms, there being at least about 8 heteroatoms, which will generally include halogen, oxygen, sulfur, nitrogen and phosphorous.

A preferred functional group may come within the following formulae:

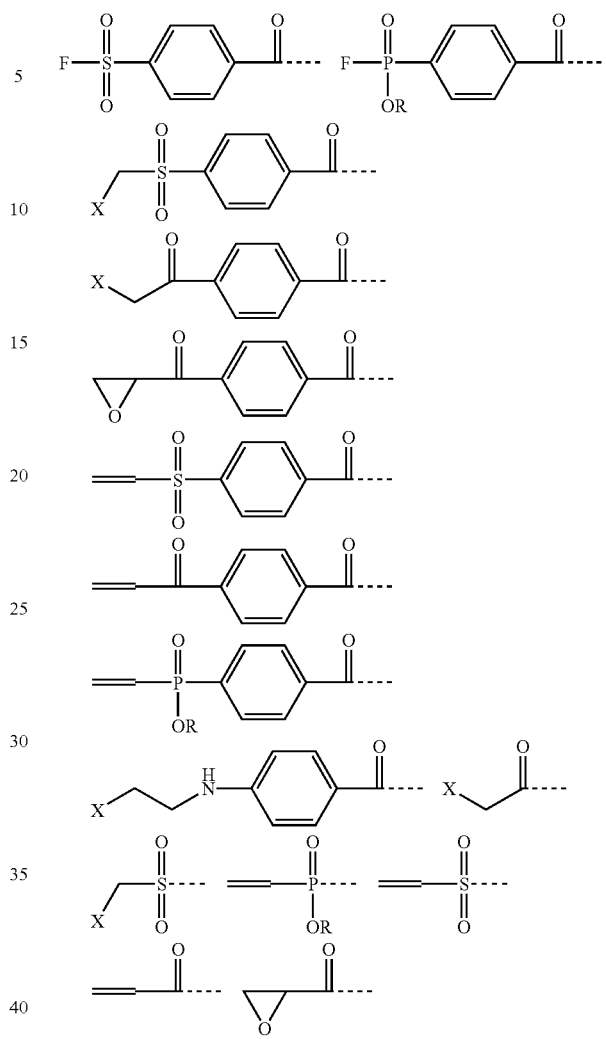

where X is halogen, particularly fluorine, chlorine, bromine or iodine.

A preferred linker moiety may come within the following formulae:

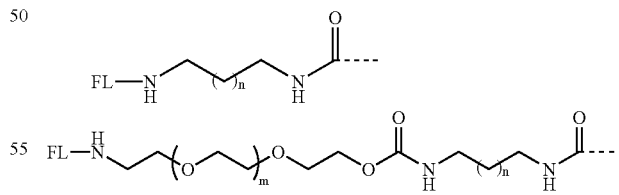

where n and m are independently in the range of 0 to 8 and.

As described above, the fluorescent moiety may be varied widely depending upon the protocol to be used, the number of different probes employed in the same assay, whether a single or plurality of lanes are used when employing electrophoresis, the availability of excitation and detection devices, and the like. Preferred fluorescent moieties may come within the following formulae:

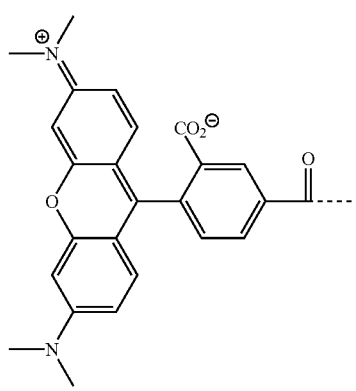

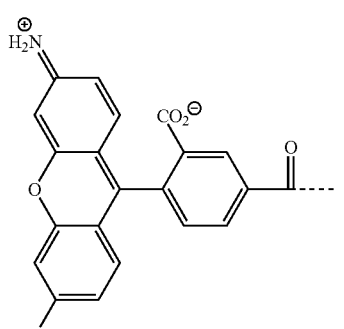

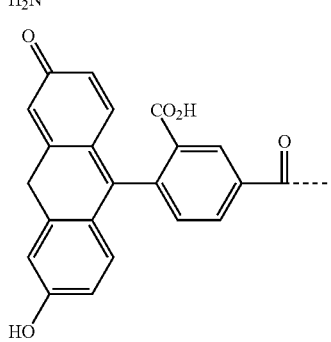

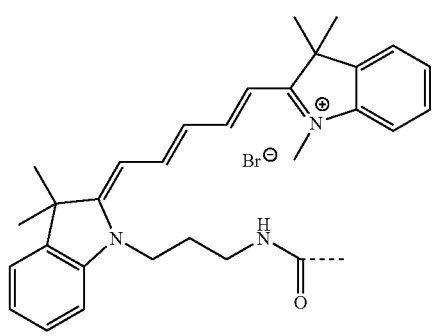

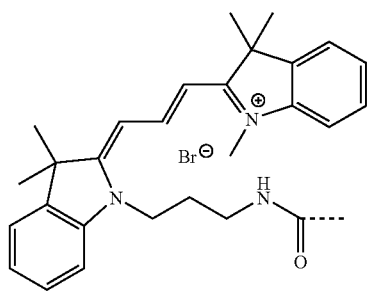

-continued

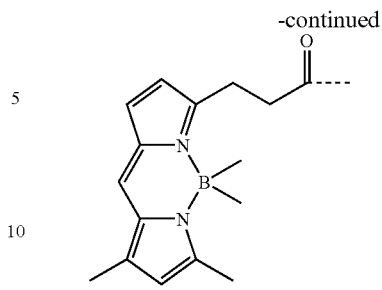

In the case of a combinatorial library, as indicated above, numerous variations as to the structure of the fABP can be prepared. These various members may then be screened with a complex protein mixture to determine which members of the library are inactive with inactivated target protein(s), but react with native protein(s). In carrying out the subject methodology, one or a plurality of fABPs may be added to a complex protein sample as described above.

In an alternative design strategy, a functional group may be selected that imparts an element of "chemical specificity" to the FABP. In these embodiments, the requirement for an affinity moiety to achieve adequate probe selectivity can be eliminated. The incorporation of an affinity moiety into a fABP can affect the number of proteins targeted by a probe. Thus, depending on the number of target proteins of interest and the similarity of active site binding selectivity, the artisan can choose to include the affinity moiety or not, as required.

For example, a fluorophosphonate reactive group provides a classical affinity label for serine hydrolases that selectively reacts with the activated serine nucleophile of catalytic triad and other serine hydrolase classes. Thus, a library of fABPs for these classes of proteins may be designed according to the following formula.

F-L-F1 wherein F is a functional group that selectively reacts with a serine residue linked to a fluorescent moiety by a linker moiety comprising from about 2 to 20, usually not more than 12, more usually not more than about 8 carbon atoms and having from 0 to 10, usually 0 to 6 heteroatoms, including O, S, N and P, where the linkage may be aliphatic, alicyclic, aromatic or heterocyclic.

A preferred functional group may come within the following formulae:

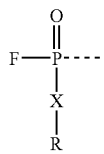

wherein X is —CH2-, —O—, or —S—;

and wherein R is H or is a chain of from 1–20 carbon atoms and from 0 to 5 heteroatoms, and may be alkyl, alkenyl, or alkynyl (each straight or branched); and may include one or more aromatic, alicyclic, heteroaromatic, or heterocyclic groups. Particularly preferred as —X—R are —O—$CH_3$, —O—$CH_2$—$CH_3$, —O—CH—$(CH_3)_2$, —CH—CH—$(CH_3)_2$, and —$CH_2$—$CH_3$.

A preferred linker moiety may come within the following formulae:

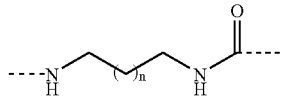

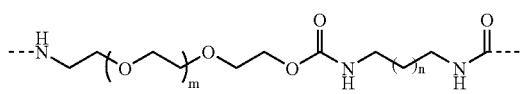

where n and m are independently in the range of 0 to 8.

A preferred fluorescent moiety may come within the following formulae:

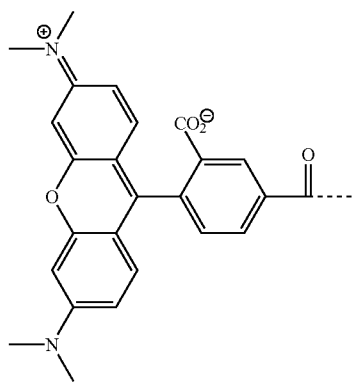

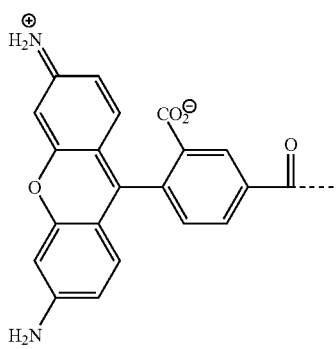

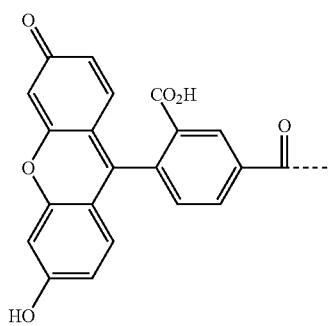

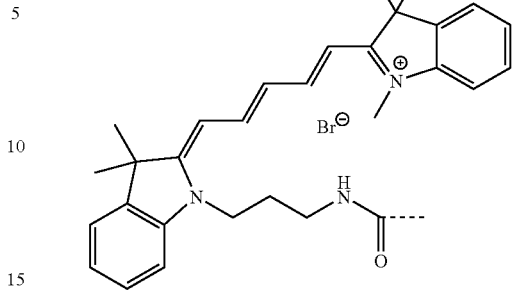

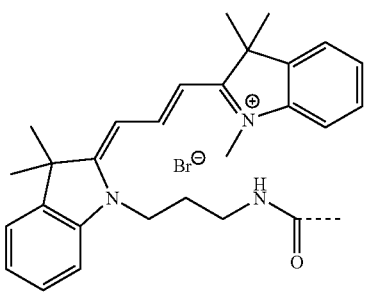

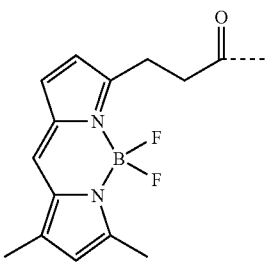

While the number of fABPs that can be used is theoretically unlimited, preferably not more than about 20 are used. Since the sources of the protein mixture will vary widely and one biomolecule may have an influence on the activity of the fABP, as well as on the reactivity of a protein, the mixture may be subject to dilution, fractionation, precipitation, extraction, dialysis, chromatography or other processing to obtain the desired composition. For the most part, the composition will not be significantly modified, maintaining substantially tile composition obtained from the source. In some instances the pH may be modified, solvents added, or the like, to enhance the reaction of the active target proteins with the fABP(s) or change the fABP profile as to the active target proteins.

Application of the FABPs to Samples

Suitable complex protein mixtures may come from different sources and be used for different purposes. In many instances, the fABPs will be used to analyze a protein mixture for active enzyme. This may include a relatively pure sample of the enzyme to determine the activity in relation to total protein of the sample. The sample may be a single cell or a mixture of cells, a neoplastic sample or other biopsy or tissue comprising a single cell type or a mixture of cell types, such as tissue from an organ, e.g. heart, lung, esophagus, kidney, brain, blood, etc., diseased tissue or healthy tissue, etc. The cells may be prokaryotic or eukaryotic, vertebrate or non-vertebrate, particularly mammalian and more particularly human. The cells or tissues, or lysates thereof, may be prepared in a variety of ways, including fractionation, using chromatography, centrifugation, fluorescence activated cell sorting, dilution, dialysis, concentration, etc. The sample will usually be treated so as to preserve the activity of the target protein(s), so that the manner of treatment will be mild, ambient or lower temperatures will be used, particularly below 37° C., and other denaturing conditions will be avoided, such as organic solvents, detergents or high salts.

Usually, a proteome will be analyzed. The term "proteome" as used herein refers to a complex protein mixture obtained from a biological sample. Preferred proteomes comprise at least about 5% of the total repertoire of proteins present in a biological sample (e.g., the cells, tissue, organ, or organism from which a lysate is obtained; the serum or plasma, etc.), preferably at least about 10%, more preferably at least about 25%, even more preferably about 75%, and generally 90% or more, up to and including the entire repertoire of proteins obtainable from the biological sample. Thus the proteome may be obtained from an intact cell, a lysate, a microsomal fraction, an organelle, a partially extracted lysate, biological fluid, and the like. The proteome will be a mixture of proteins, generally having at least about 20 different proteins, usually at least about 50 different proteins and in most cases 100 different proteins or more.

Generally, the sample will have at least about $1 \times 10^{-11}$ g of protein, and may have 1 g of protein or more, preferably at a concentration in the range of about 0.1–10 mg/ml. For screening applications, the sample will typically be between about $1 \times 10^{-11}$ g and about $1 \times 10^{-3}$ g of protein, preferably between about $1 \times 10^{-6}$ g and $1 \times 10^{-4}$ g of protein. For identification of labeled active target proteins, the sample will typically be between about $1 \times 10^{-9}$ g and about 1 g of protein, preferably between about $1 \times 10^{-4}$ g and $1 \times 10^{-1}$ g of protein. The term "about" in this context refers to +/−10% of the amount listed.

The sample may be adjusted to the appropriate buffer concentration and pH, if desired. One or more fABPs may then be added, each at a concentration in the range of about 1 nM to 20 mM, preferably 10 nM to 1 mM, most preferably 10 nm to 100 μM. After incubating the reaction mixture, generally for a time for the reaction to go substantially to completion, generally for about 0.11–60 minutes, at a temperature in the range of about 5–40° C., preferably about 10° C. to about 30° C., most preferably about 20° C., the reaction may be quenched. Since the extent of the reaction will increase with time, the longer the time, the more cross-reactivity may be anticipated. Therefore, relatively short reaction times may be used. One can standardize the amount of reaction with a known amount of added target protein to the sample and run rate studies to determine the optimum time for the reaction. Once this is done with all of the targets, a preferred time will be employed to provide the most favorable results, that is, the greatest level of reaction with the target proteins with the least cross-reactivity. At the end of the reaction time, the mixture is then ready to be used for electrophoresis, e.g. in screening applications.

In one aspect of the invention, the method provides for quantitative measurement of active target proteins in biological fluids, cells or tissues. Moreover, the same general strategy can be broadened to achieve the proteome-wide, qualitative and quantitative analysis of the state of activity of proteins, by employing fABPs or libraries of fABPs with differing specificity for reaction with proteins. The method and reagents of this invention can be used to identify proteins of low abundance that are active in complex mixtures and can be used to selectively analyze specific groups or classes of proteins, such as membrane or cell surface proteins, or proteins contained within organelles, sub-cellular fractions, or biochemical fractions such as immunoprecipitates. Further, these methods can be applied to analyze differences in expressed proteins in different cell states. For example, the methods and reagents herein can be employed in diagnostic assays for the detection of the presence or the absence of one or more active proteins indicative of a disease state, such as cancer.

The fABPs may be a single fABP that usually binds to at least 5, more usually at least about 10, different active target proteins or may be a mixture of fABPs that bind to the same number or fewer proteins and may bind to proteins that are not related by a particular known family relationship. While only one probe need be used with a test sample, a mixture of probes can have from about 2–20, more usually 2–15, frequently from about 2 to 6, different fABPs selected to target a multiplicity of active proteins. Usually, there will be the capability of binding to at least 5 different proteins, frequently at least 10 different proteins, more usually at least about 15 different proteins and the number of different proteins capable of being bound, may be 20 or more. Frequently at least one fABP in a mixture will be capable of bonding to at least about 5 different target proteins.

For reacting with the active form of a class of proteins (i.e., proteins having a known family relationship, such as kinases, serine hydrolases, etc.), it is desirable that one employs a functionality that is specific for the target protein genus. For many of the enzyme genera, functionalities are known that do not significantly react with enzymes of other genera, particularly non-enzymatic proteins and enzymes that have different reactive sites. Methods as those described in this application are employed to distinguish this non-active site labeling from activity-dependent labeling of the active site.

As discussed above, it is desirable that the fABP does not react with inactive target proteins. Examples of inactive states include: 1) proenzymes, e.g. requiring cleavage of the protein; 2) enzymes bound by endogenous inhibitors (either covalent or non-covalent); 3) enzymes in an inactive conformation (e.g. enzymes that require the binding of another protein, a conformational change, covalent modification by either phosphorylation, reduction, oxidation, methylation, oracylation (e.g. by formic or acetic acid) for conversion to an active state; 4) denatured enzymes; 5) mutant enzymes; 6) enzymes bound by either reversible or irreversible exogenous inhibitors; and 7) enzymes requiring a cofactor for activity.

The target proteins will usually have at least one of serine, threonine, tyrosine, cysteine, histidine, lysine, arginine, aspartate or glutamate located in or near the active site, preferably involved in the catalysis of an enzymatic reaction.

Enzymes of interest may fall within six main classes: oxidoreductases, transferases, hydrolases, lyases, isomerases and ligases. Exemplary oxidoreductases include cytochrome P450s, amine oxidases, alcohol dehydrogenases, aldehyde dehydrogenases, such as ALDH1, ALDH2, ALDH3, desaturases, etc. Exemplary enzymes include serine hydrolases, which includes sub-genera such as proteases, e.g. trypsins, chymotrypsins, esterases, such as acetylcholinesterases, thioesterases, amidases, such as FAAH, and acylpeptide hydrolases, lipases, transacylases, such as lecithin:cholesterol acyltransferase; cysteine hydrolases, such as caspases, cathepsins, and palmitoyl acyltransferases;

and metallohydrolases, including matrix metalloproteinases ("MMPs"), e.g. MMP1–13, membrane type metalloproteinases, aminopeptidases, and ADAMalysins.

Additional enzymes of interest include phosphatases, such as alkaline phosphatases, acid phosphatases, protein tyrosine phosphatases, and serine/threonine phosphatases; GTPases; ATPases; kinases, which include enzymes such as tyrosine kinases, e.g. src, abl, and lck, serine/threonine kinases, e.g. MAP kinases, MAPK kinases, CAM kinases, protein kinase C, and casein kinases; receptors, such as HLA antigens, hormone receptors, and G-proteins coupled receptors; ion channels; transcription factors; protease inhibitors and the like.

Known serine hydrolases include fatty acid amide hydrolases (FAAH), kallikreins, acylpeptide hydrolases, prostate specific antigen, cholinesterases, trypsins, chymotrypsins, plasmin, thrombin, phospholipases, signal peptidases, amidase signature enzymes, plasminogen activators, prohormone convertases, granzymes, seprase, dipeptidyl and tripeptidyl peptidases, usually being derived from mammalian sources, particularly human, but may come from other sources, both prokaryotic and eukaryotic, including plants, birds, invertebrates, fungi, etc.

Exemplary inactivating conditions include chemical or physical means for inactivating, normally by denaturing the protein. For example, chemical means include denaturants such as organic solvents, harsh detergents, e.g. SDS, chaotropic agents, e.g. urea, guanidinium chloride or isocyanate, etc., and other denaturing agents. Physical means include heat, freezing, electromagnetic radiation, shearing, drying, electrical discharge and the like. Inactivating agents that bind to the active site or an allosteric site affecting activity may bind covalently or non-covalently, with non-covalent binding being preferable.

Candidate compounds to be used as therapeutics associated with indications involving enzyme dysfunction, particularly for inhibiting specific or groups of related enzymes, may be monitored by preparing a reaction mixture with one or more related enzymes and monitoring the effect on the rate of fABP labeling. One would add one or more fABPs, together with one or more candidate compounds, and then monitor the rate of fABP labeling, e.g., by isolating aliquot (s) and analyzing the aliquot for enzyme activity or fABP labeling.

Analysis of Samples for FABP Signals

The term "separating" as used herein refers to methods that enrich the concentration of a molecule of interest in a particular location or container relative to other molecules originally present. For example, gel electrophoresis enriches the concentration of molecules that migrate at a particular rate relative to other molecules originally present that migrate at different rates; sequestration methods enrich the concentration of molecules capable of being sequestered (e.g., by binding to a receptor) relative to other molecules not so capable (e.g., removed by washing out molecules that do not bind to a receptor). Numerous additional analytical procedures are known to the artisan for separating and analyzing complex protein mixtures (e.g., chromatographic methods such as HPLC, FPLC, ion exchange, size exclusion; mass spectrometry; differential centrifugation).

In preferred embodiments, the probe products are analyzed by electrophoresis, e.g. slab gel, capillary or microfluidic, optionally using a gel for separation of the different components. In particularly preferred embodiments, SDS-PAGE is used, including 2D PAGE. The sample composition may be preliminarily separated using isoelectric focusing, followed by using bands or regions for further electrophoretic separation. Conventional conditions can be employed for the electrophoresis, using a denaturing medium, so that the active sample and the inactivated sample are both denatured in the gel. Numerous patents have issued for performing electrophoresis for the separation of proteins. See, e.g., U.S. Pat. Nos. 4,415,655; 4,481,094; 4,865,707; and 4,946,794. Texts describing procedures include Laemmli, UK, Nature (1970) 227, 680–685; Sambrook, J.; MacCallum, P. & Russell, D. (2001) "Molecular Cloning: A Laboratory Manual." $3^{rd}$ Edition, Cold Spring Harbor Press, Cold Spring Harbor, N.Y.

In designing a gel-based analysis system, the artisan may balance various considerations, such as speed, resolution, sample volume, choice of fluorophore, detection methods, etc. in order to arrive at an optimal solution. For example, for simple screening analysis (i.e., when gel bands are not to be identified by means of eluting proteins from the gel matrix for further analysis), very thin gels may be run quickly. Additionally, such thin gels are amenable to the use of laser-induced fluorescence scanning systems and narrow gel lanes, as laser focusing and confocal detection optics permit the detection of very small amounts of fABP in a sample. Conversely, thicker gels may be advantageous in protein identification analysis, as a sufficient amount of material must be obtained from a gel band to permit further manipulations.

For rapid screening analysis, a suitable gel electrophoresis platform would consist of a glass sandwich gel format of from 15–40 cm in width, 20–40 cm in length, and from 0.6 to 0.2 cm in thickness. A partciularly preferred format is from about 30–35 cm in width, about 25–30 cm in length, and about about 0.4 mm in thickness. The term "about" in this context refers to +/−10% of a given dimension. The gel format is preferably combined with a laser-induced fluorescence detector apparatus comprising detection optics that permit sampling of the gel without removal from the gel plates, as such thin gels may be extremely fragile. Typically, such an instrument uses confocal optics for detection. By matching the thickness of the gel to the thickness of the confocal "slice," signal detection can be matched to a minimal amount of sample.

The spacing between sample wells is limited only by the amount of sample necessary to obtain a sufficient signal for measurement. Appropriate spacings are between 1 and 4 mm, most preferably about 2.25–3 mm. The term "about" in this context refers to +/−10% of the spacing between wells. Selecting a spacing between wells of about 2.25 mm as an example, a gel platform 25 cm in width could accommodate as many as 96 individual samples.

The subject invention allows for adding more than one sample to the same lane (including a single capillary), so that one can obtain a result from two or more samples in a single run. In this way, the test sample and the control sample can be mixed, where the fABPs in the two samples have different fluorescent groups that allow for individual detection. As discussed above, it is desirable that the fluorophores do not significantly affect the electrophoretic migration of the proteins to which they are attached However, since the fluorophore may provide only a small change in the molecular weight of the labeled proteins (this will be different if one uses protein fragments) and the denaturant provides the charge, relatively substantial differences in composition between the fluorophores can be tolerated. For the most part, even when the two fluorophores can have energy transfer, this is not likely to significantly interfere with the fluorescent measurement in a single band containing both fluorophores.

After completing the electropherogram, the bands may then be read using any convenient fluorescent reader, e.g. Hitachi FMbio Flatbed Fluorescence Scanner, where the intensity of each band may be transferred to a data processor for processing. Depending on whether one or more lanes are involved with the analysis, the data may be compiled from a single or multiple lanes to establish the bands associated with active target proteins that are absent with the inactive sample, the different target proteins that reacted with different probes as evidenced by the different fluorescence emission for each of the probes, and any cross-reactivity between the probes. The bands that are obtained in the gel are sharp and provide for excellent resolution. Particularly, much better resolution and sensitivity may be obtained than when biotin-labeled probes are used, followed by complex formation with labeled avidin, and Western blotting.

Fluorescent energy transfer methods can also be used to distinguish what might otherwise be considered identical species. Fluorescence resonance energy transfer is used as follows: Individual proteins or peptides are labeled with a second reactive moiety (e.g., an iodoacetamide or NHS ester) that carries a reporter fluor (e.g., rhodamine, if the primary labeling is carried out using fluorescein). Since the FRET measurement is sensitive to the distance between the fluors, the relative intensities of emission is a fingerprint of the particular protein or peptide. Other methods that are used include fluorescence correlation (see, e.g., Wang, G. and Geng, L. (2000) Anal. Chem. 72, 4531–4542), fluorescence polarization, fluorescence lifetime measurements, etc., effectively improving the resolution of the separation methods. These techniques serve to reduce background from the gel, further enhancing resolution and detection.

The following examples are offered by way of illustration and not by way of limitation.

EXAMPLES

Example 1

Compound 1a is the starting material tetraethyleneoxy (3,6,9-oxa-1,11-diolundecane) and compound 1b is the stating material decylene-1,10-diol as depicted in the flow chart in FIG. 1.

Preparation of triethyleneoxy-linked fluorophosphonate and N-fluorescer-formamidoalkylenecarbamoyl (where the fluorescer is BODIPY(FL) or tetramethylrhodamine and the alkylene is 2 or 5 carbon atoms respectively), or N-fluorescein thioureidopentanylcarbamoyl, where the fluorescer in this example is fluorescein. The other fluorescer compounds are made in substantially the same way, using the different fluresceralkylamino derivatives as shown in the flow chart.

Compound 2. A solution of 1 (3.9 g, 20.0 mmol, 3.0 equiv) in DMF (8.0 mL) was treated with TBDMSCl (1.0 g, 6.64 mmol, 1.0 equiv) and imidazole (0.9 g, 13.3 mmol, 2.0 equiv) and the reaction mixture was stirred for 12 h at room temperature. The reaction mixture was then quenched with saturated aqueous NaHCO3 and partitioned between ethyl acetate (200 mL) and water (200 mL). The organic layer was washed with dried (Na2SO4) and concentrated under reduced pressure. Chromatography (SiO2, 5×15 cm, 50–100% ethyl acetate-hexanes) afforded 2 (1.1 g, 2.0 g theoretical, 55%) as a colorless oil: 1H NMR (CDCl3, 400 MHz) δ 3.8–3.5 (m, 16H, CH2OR), 0.88 (s, 9H, CH3C), 0.0 (s, 6H, CH3Si).

Compound 3. A solution of 2 (0.61 g, 2.0 mmol, 1.0 equiv) in benzene (15 mL, 0.13 M) was treated sequentially with PPh3 (2.6 g, 10.0 mmol, 5 equiv), I2 (2.3 g, 9.0 mmol, 4.5 equiv), and imidazole (0.7 g, 10.3 mmol, 5.2 equiv) and the reaction mixture was stirred at room temperature for 30 min, producing a yellow-orange heterogeneous solution. The soluble portion of the reaction mixture was removed and the insoluble portion washed several times with ethyl acetate. The combined reaction and washes were then partitioned between ethyl acetate (200 mL) and saturated aqueous Na2S2O3 (200 mL). The organic layer was washed sequentially with H2O (100 mL) and saturated aqueous NaCl (100 mL), dried (Na2SO4), and concentrated under reduced pressure. Chromatography (SiO2, 5×15 cm, 5–25% ethyl acetate-hexanes) afforded 3 (0.54 g, 0.82 g theoretical, 66%) as a colorless oil: 1H NMR (CDCl3, 400 MHz) δ 3.85–3.60 (m, 12H, CH2OR), 3.54 (t, J=5.6, 2H, CH2OTBDMS), 3.23 (t, J=7.0 Hz, 2H, CH2I), 0.88 (s, 9H, CH3C), 0.0 (s, 6H, CH3Si).

Compound 4. Triethylphosphite (1.2 mL, 7.0 mmol, 5.4 equiv) was added to 3 (0.53 g, 1.29 mmol, 1.0 equiv) and the mixture was stirred at 150° C. for 1 h. The reaction mixture was cooled to room temperature and directly submitted to flash chromatography (SiO2, 5×15 cm, 100% ethyl acetate) to afford 4 (0.43 g, 0.54 g theoretical, 80%) as a colorless oil: 1H NMR (CDCl3, 400 MHz) δ 4.20–4.05 (m, 4H, CH3CH2OP), 3.80–3.55 (m, 14H, CH2OR), 2.15 (m, 2H, CH2P), 1.31 (t, J =6.0 Hz, 6H, CH3CH2OP), 0.88 (s, 9H, CH3C), 0.0 (s, 6H, CH3Si).

Compound 5. A solution of compound 4 (0.21 g, 0.5 mmol, 1.0 equiv) in CH2Cl2 (2.8 mL, 0.18 M) was treated with HF-pyridine (0.084 mL, ~0.84 mmol, ~1.7 equiv). The reaction was stirred at 25° C. for 30 min and then partitioned between ethyl acetate (100 mL) and water (100 mL). The organic layer was dried (Na2SO4) and concentrated under reduced pressure. Chromatography (SiO2, 2×8 cm, 3–10% CH3OH—CH2Cl2) afforded 5 (0.050 g, 0.28 g theoretical, 32.5%) as a clear oil: 1H NMR (CDCl3, 400 MHz) δ 4.20–4.05 (m, 4H, CH3CH2OP), 3.80–3.55 (m, 14H, CH2OR), 2.15 (m, 2H, CH2P), 1.31 (t, J=6.0 Hz, 6H, CH3CH2OP); MALDI-FTMS m/z 337.1377 (Cl2H27O7P+ Na+ requires 337.1387).

Compound 6. A solution of 5 (0.030 g, 0.096 mmol, 1.0 equiv) in DMF (0.28 mL, 0.34 M) was treated sequentially with N,N-disuccinimidyl carbonate (0.058 g, 0.22 mmol, 2.2 equiv) and triethylamine (0.035 μL, 0.25 mmol., 2.5 equiv) and triethylamine (0.035 μL, 0.25 mmol., 2.5 equiv), The reaction mixture was stirred at room temperature for 12 h and then partitioned between CH2Cl2 (100 mL) and H2O (100 mL). The organic layer was washed with saturated aqueous NaCl (100 mL), dried (Na2SO4), and concentrated under reduced pressure. Chromatography (SiO2, 2×8 cm, 1–10% CH3OH—CH2Cl2) afforded 50.035 g, 0.043 g theoretical, 81%) as a clear oil: 1H NMR (CDCl3, 400 MHz) δ 4.45 (m, 2H, CH2OC(O)OR), 4.20–4.05 (m, 4H, CH3CH2OP), 3.80–3.55 (m, 12H, CH2OR), 2.84 (s, 4H, CH2C(O)N), 2.15 (m, 2H, CH2P), 1.31 (t, J=6.0 Hz, 6H, CH3CH2OP). MALDI-FTMS m/z 478.1456 (C17H30NO11P+Na+ requires 478.1449).

Compound 7. A solution of 6 (0.020 g, 0.044 mmol, 1.0 equiv) in CH2Cl2 (0.14 mL, 0.40 M) was cooled to 0° C. and treated with oxalyl chloride (0.082 mL, 2M in CH2Cl2, 0.164 mM 3.7 equiv). The reaction mixture was allowed to warm to room temperature and stirred for 18 h. The reaction mixture was then concentrated under a stream of gaseous nitrogen and the remaining residue treated with H2O (0.1 mL) for 5 min. The H2O was evaporated under a stream of gaseous nitrogen and the remaining residue dried by vacuum to provide 7 (0.015 mg, 0.019 mg theoretical, 80%) as a clear oil/film: 1H NMR (CDCl3, 400 MHz) δ 4.45 (m, 2H, CH2OC(O)OR), 4.10 (m, 2H, CH3CH2OP), 3.80–3.55 (m, 12H, CH2OR), 2.84 (s, 4H, CH2C(O)N), 2.15 (m, 2H, CH2P), 1.31 (t, J=6.0 Hz, 3H, CH3CH2OP).

Compound 8. A solution of 7 (0.007 g, 0.016 mmol, 1.0 equiv) in CH2Cl2 (0.22 mL, 0.075 M) at −78° C. was treated with (diethylamino)sulfur trifluoride (DAST, 0.007 mL, 0.048 mmol, 3.0 equiv) and the reaction mixture was stirred for 10 min. The reaction mixture was then partitioned between ethyl acetate (100 mL) and H2O (100 mL) and the organic layer was washed with saturated aqueous NaCl (100 mL), dried (Na2SO4), and concentrated under reduced pressure. Chromatography (SiO2, Pasteur pipette, 100% ethyl acetate) afforded 8 (0.003 g, 0.007 g theoretical, 42%) as a clear oil: 1H NMR (CDCl3, 400 MHz) δ 4.45 (m, 2H, CH2OC(O)OR), 4.27 (m, 2H, CH3CH2OP), 3.80–3.55 (m, 12H, CH2OR), 2.84 (s, 4H, CH2C(O)N), 2.32–2.26 (m, 2H, CH2P), 1.31 (t, J=6.0 Hz, 3H, CH3CH2OP).

Compound 9. A solution of tetramethylrhodamine cadaverine (Molecular Probes, Eugene, Oreg.) (0.005 g, 0.010 mmol, 1.0 equiv) in DMF (0.5 mL, 0.020 M) was added to compound 8 (neat, 0.007 g, 0.016 mmol, 1.7 equiv) and the reaction mixture was stirred for 30 min at room temperature. The solvent was removed under vacuum and the products were resuspended in a 0.35 mL of a water-acetonitrile mixture (1:1 v./v.) containing 0.1% (v./v.) trifluoroacetic acid. An aliquot of this solution (0.30 mL) was injected on a preparative reverse phase HPLC column (Haisil 100 C8, Higgins Analytical, 20 mm×150 mm), separated using a 0–100% acetonitrile gradient in 30 minutes at 10 mL per min. The retention time under these conditions was 19.95 min. The solvent was removed under vacuum using a rotary evaporator, and afforded 9 (0.0035 g, 0.0042 mmol, 42%) as a darkly colored oil.: $^1$H-NMR (d$_6$-DMSO, 250 MHz) δ 8.87 (m, 1H), 8.70 (s, 1H, ArH), 8.28 (d, 2H, ArH), 7.55 (d, 2H, ArH), 7.05–6.9 (m, 3H, ArH), 4.25–4.10 (m, 2H, POCH$_2$CH$_3$), 4.05–3.95 (m, 2H, CH$_2$OCONH), 3.7–3.55 (m, 2H, PCH$_2$CH$_2$O), 3.27–3.12 (m, 2H, CH$_2$NCO), 3.05–2.9 (m, 2H, CONHCH$_2$), 2.45–2.25 (m, 2H, PCH$_2$), 1.65–1.3 (m, 6H), 1.26 (t, J=6.9 Hz, 3H, CH$_3$CH$_2$OP).

FP-alkyleneamino-fluorescer was prepared as described by Liu et al. (Proc. Natl. Acad. Sci. 96(26):14694, 1999) and in U.S. Ser. Nos. 60/195,954 and 60/212,891, herein incorporated by reference in their entirety. 1-Iodo-10-undecene (3). A solution of 2 (3.4 g, 10.5 mmol, 1.0 equiv) in acetone (21 mL, 0.5 M) was treated with NaI (3.2 g, 21 mmol, 2.0 equiv) and the reaction mixture was stirred at reflux for 2 h, producing a yellow-orange solution. The reaction mixture was then partitioned between ethyl acetate (200 mL) and water (200 mL). The organic layer was washed sequentially with saturated aqueous Na2S2O3 (100 mL) and saturated aqueous NaCl (100 mL), dried (Na2SO4), and concentrated under reduced pressure. Chromatography (SiO2, 5×15 cm, 1–2% ethyl acetate-hexanes) afforded 3 (2.3 g, 2.9 g theoretical, 78%) as a colorless oil: 1H NMR (CDCl3, 250 MHz) δ 5.95–5.75 (m, 1H, RCH═CH2), 5.03–4.90 (m, 2H, RCH═CH2), 3.16 (t, J=7.0 Hz, 2H, CH2I), 2.02 (m, 2H, CH2CH═CH2), 1.80 (p, J=6.9 Hz, 2H, CH2CH2I), 1.50–1.20 (m, 12H).

1-[Bis(ethoxy)phosphinyl]-10-undecene (4). Triethylphosphite (12.2 mL, 71 mmol, 10 equiv) was added to 3 (2.0 g, 7.1 mmol, 1.0 equiv) and the mixture was stirred at reflux for 15 h. The excess triethylphosphite was removed by distillation and the remaining residue submitted to flash chromatography (SiO2, 5×15 cm, 25–50% ethyl acetate-hexanes gradient elution) to afford 4 (1.30 g, 2.1 g theoretical, 62%) as a colorless oil: 1H NMR (CDCl3, 250 MHz) δ 5.95–5.75 (m, 1H, RCH═C═CH2), 5.03–4.90 (m, 2H, RCH═CH2), 4.05 (m, 4H, CH3CH2OP), 2.02 (m, 2H, CH2CH═CH2), 1.80–1.20 (m, 20H); MALDI-FTMS (DHB) m/z 291.2088 (C15H31O3P+H+ requires 291.2089).

1-(Ethoxyhydroxyphosphinyl)-10-undecene (5). A solution of compound 4 (0.31 μg, 1.07 mmol, 1.0 equiv) in CH2Cl2 (4.0 mL, 0.3 M) was treated dropwise with trimethylsilyl bromide (TMSBr, 0.17 mL, 1.28 mmol, 1.2 equiv). The reaction was stirred at 25° C. for 1 h, quenched with 5 mL of 5% [w/v] KHSO4, and stirred vigorously for 5 minutes. The reaction mixture was then partitioned between ethyl acetate (100 mL) and water (100 mL), and the organic layer was washed with saturated aqueous NaCl (200 mL), dried (Na2SO4), and concentrated under reduced pressure. Chromatography (SiO2, 2×8 cm, 12–20% CH3OH—CHCl3 with 1% aqueous NH4OH) afforded 5 (0.10 g, 0.28 g theoretical, 36.2%; most of the remaining mass was recovered as starting material) as a clear oil: 1H NMR (CDCl3, 250 MHz) δ 5.95–5.75 (m, 1H, RCH═CH2), 5.03–4.90 (m, 2H, RCH═CH2), 4.05 (m, 2H, CH3CH2OP), 2.02 (m, 2H, CH2CH═CH2), 1.80–1.20 (m, 20H). MALDI-FTMS (DHB) m/z 285.1589 (C13H27O3P+Na+ requires 285.1596).

10-(Ethoxyhydroxyphosphinyl)-decanoic acid (6). Compound 5 (0.10 g, 0.38 mmol, 1.0 equiv) in a biphasic solution composed of CCl4-CH3CN—H2O (1.0 mL-1.0 mL-1.5 mL; total volume of 3.5 mL, 0.11 M) was treated sequentially with sodium periodate (0.31 g, 1.56 mmol, 4.1 equiv) and ruthenium trichloride hydrate (0.002 g, 0.009 mmol, 0.022 equiv). The reaction mixture was stirred at 25° C. for 2 h and then partitioned between CH2Cl2 (50 mL) and 1 N aqueous HCl (50 mL). The organic layer was washed with saturated aqueous NaCl (25 mL), dried (Na2SO4), and concentrated under reduced pressure. The resulting residue was resuspended in 40 mL of diethyl ether, filtered through a Celite pad, and concentrated under reduced pressure to afford 6 (0.09 g, 0.11 g theoretical, 83%) as a colorless semisolid: 1H NMR (CDCl3, 250 MHz) δ 4.05 (m, 2H, CH3CH2OP), 2.32 (t, J=7.5 Hz, 2H, CH2COOH), 1.80–1.20 (m, 16H); FAB-HRMS (NBA-NaI) m/z 303.1340 (C12H25O5P+Na+ requires 303.1337).

FP-fluorescer, or 10-(fluoroethoxyphosphinyl)-N-(fluoresceramidopentyl)-decanamide (7). A solution of 6 (0.007 g, 0.025 mmol, 4.0 equiv) in CH2Cl2 (0.4 mL, 0.06 M) at −78° C. was treated dropwise with (diethylamino)sulfur trifluoride (DAST, 0.021 mL, 0.10 mmol, 4.0 equiv), brought to 25° C., and stirred for 5 min. The reaction mixture was then treated with one-half reaction volume of dimethyl formamide containing N-hydroxysuccinimide (0.05 g, 0.25 mmol, 10 equiv) and stirred for an additional 10 min at 25° C. The reaction mixture was then partitioned between ethyl acetate (50 mL) and water (50 mL), and the organic layer was washed with saturated aqueous NaCl (200 mL), dried (Na2SO4), and concentrated under reduced pressure to afford 10-(fluoroethoxyphosphinyl)-N-(hydroxysuccinyl)-decanamide (as judged by crude 1H NMR;). Without further purification, this compound was treated with 5-(fluoresceramido)-pentylamine (Pierce, 0.0021 g, 0.062 mmol, 1.0 equiv) in MeOH (0.02 mL) and stirred for 10 min. The solvent was evaporated under a stream of gaseous nitrogen and the remaining residue was washed sequentially with diethyl ether and ethyl acetate, solubilized in a minimal volume of chloroform, transferred to a clean glass vial, and the solvent evaporated. This process was repeated once more to rid the desired product of excess reagents and byproducts, affording the desired product in substantially pure form.

Preparation of Pyridylsulfonate-decylene-tetramethylrhodamine Probe

All reactions were carried out under an atmosphere of argon unless specified. Methylene chloride ($CH_2Cl_2$) was dried by passing through activated alumina columns. Commercial reagents of high purity were purchased and used without further purification unless otherwise noted. NMR spectra were obtained on a Bruker AMX-400 instrument and calibrated to the residual solvent peak. The multiplicities are abbreviated as follows: s=singlet, d=doublet, t=triplet, q=quartet, p=pentet, m=multiplet).

((2-Pyridylsulfonyl)oxo)-10-undecene (13): A solution of ω-undecylenyl alcohol (12)(0.50 g, 2.91 mmol, 1.0 equivalents (equiv.)) in pyridine (4 mL) was cooled to 0° C. and treated with 2-pyridylsulfonyl chloride (1.04 g, 5.87 mmol, 2.0 equiv.), prepared according to the procedure of Corey and colleagues [Corey, et al. (1989). J. Org. Chem. 54, 389–93]. The reaction mixture was kept at 0° C. for 6 hours, then partitioned between ethyl acetate (50 mL) and water (25 mL). The organic layer was washed with 10% aqueous HCl (2×50 mL) and saturated aqueous NaCl (50 mL), dried (MgSO4), and concentrated under reduced pressure. Column chromatography (2% EtOAc/Hex) afforded 13 as a colorless oil (98%): $^1$H NMR ($CDCl_3$, 400 MHz) δ 8.61 (m, 1H, ArH), 7.89 (m, 2H, ArH), 7.47 (m, 1H, ArH), 5.67–5.60 (m, 1H, RCH=$CH_2$), 4.84–4.74 (m, 2H, RCH=$CH_2$), 4.21 (t, J=6.4 Hz, 2H, $CH_2OSO_2Pyr$), 1.88 (m, 2H $CH_2CH$=$CH_2$), 1.55 (p, 2H, J=6.8 Hz, 2H, $CH_2CH_2OSO_2Pyr$), 1.20–1.08 (m, 12H); matrix-assiste, laser desorption ionization (MALDI)-FTMS 334.1433 ($C_{16}H_{25}NO_3S+Na^+$ requires 334.1447).

10-((2-Pyridylsulfonyl)oxo)-decanoic acid (14): Compound 13 (0.90 g, 2.88 mmol, 1 equiv.) in a biphasic solution composed of $CCl_4$-$CH_3CN$—$H_2O$ (10 mL-10 mL-15 mL) with a total volume of 35 mL was treated sequentially with sodium periodate (2.53 g, 11.80 mmol, 4.1 equiv.) and ruthenium trichloride hydrate (0.005 g, 0.02 mmol, 0.03 equiv.). The reaction was stirred at 25° C. overnight then partitioned between $CH_2Cl_2$ (100 mL) and 1N aqueous HCl (2×100 mL). The organic layer was washed with saturated aqueous NaCl (100 mL), dried ($MgSO_4$) and concentrated under reduced pressure. Column chromatography (40% EtOAc/Hex) afforded 14 (80%): $^1$H NMR ($CDCl_3$, 400 MHz) δ 8.84 (d, J=4.0 Hz. 1H. ArH), 8.11 (d, J=5.9 Hz, 1H, ArH), 8.05 (t, J=6.0 Hz, 1H, ArH), 7.65 (t, J=3.3 Hz, 1H, ArH), 4.37 (t, J=6.6 Hz, 2H, $CH_2OSO_2Pyr$), 2.34 (t, J=7.4 Hz, 2H, $CH_2COOH$), 1.70 (p, J=8.0 Hz, 2H, $CH_2CH_2COOH$), 1.61 (p, J=7.3 Hz, 2H, $CH_2CH_2OSO_2Pyr$), 1.25 (m, 10H): MALDI-FTMS (DHB) m/z 352.1202 ($C_{15}H_{23}NO_5S+Na^+$ requires 352.1189).

10-((2-Pyridylsulfonyl)oxo)-N-tetramethylrhodaminepentyldecanamide (1): A solution of 14 (0.030 g, 0.09 mmol, 10 equiv.) in $CH_2Cl_2$ (1.5 mL) at −78° C. was treated dropwise with (diethylamino)sulfur trifluoride (0.027 mL, 0.21 mmol, 22 equiv.), brought to 25° C., and stirred for 10 minutes. The reaction was then treated with one-half reaction volume of dimethylformamide containing N-hydroxysuccinimide (0.05 g, 0.04 mmol, 40 equiv.) and stirred for an additional 15 min at 25° C. The reaction mixture was partitioned between ethyl acetate (50 mL) and water (50 mL). The organic layer was washed with saturated aqueous NaCl (200 mL), dried ($Na_2SO_4$), and concentrated under reduced pressure to afford 10-((2-pyridylsulfonyl)oxo)-N-(hydroxysuccinyl)decanamide (as judged by crude $^1$H NMR; data not shown). Without further purification, the intermediate was treated with tetramethylrhodamine cadaverine (0.005 g, 0.01 mmol, 0.11 eq; Molecular Probes, Eugene, Oreg.) in DMF1 (0.5 mL) and stirred for 30 min. The solvent was removed under vacuum and the products were resuspended in a 0.35 mL of a water-acetonitrile mixture (1:1 v./v.) containing 0.1% (v./v.) trifluoroacetic acid. An aliquot of this solution (0.30 mL) was injected on a preparative reverse phase HPLC column (Haisil 100 C8, Higgins Analytical, 20 mm×150 mm), separated using a 0–100% acetonitrile gradient in 30 minutes at 10 mL per min. The retention time under these conditions was 21.15 min. The solvent was removed under vacuum using a rotary evaporator, and afforded product (0.0014 g, 0.0016 mmol, 16%) as a darkly colored oil.

Example 2

Proteome Analyses

Proteomes of rat testis were prepared as follows: Frozen rat tissues were purchased from Pel-Freeze Corporation. The tissues were diced into cubes (1 mm) and placed in Tris buffer (50 mM, pH 8) containing sucrose (320 mM). The tissues were then disrupted using a Tissue Tearor (BioSpee Products). The suspension was then filtered through cheesecloth and homogenized (Dounce). The tissue extracts were then clarified by sequential centrifugation (spin 1 1,100×g, 5 min; spin 2, 22,000×g, 30 min; and spin 3, 105,000×g, 60 min). The supernatant from the final spin constituted the cytoplasmic protein fraction of the proteome. For further analysis, protein concentrations were determined using the $D_c$ Protein Assay Kit (Bio-Rad). The concentration of final supernatants were adjusted to 1.5 mg/ml prior to storage at −80° C.

Proteomes of COS-7 cells were prepared as follows: COS-7 cells were grown in a 10 cm round petri plate in RPMI-1640 media containing 10% fetal calf serum. The cells were grown to confluence, the media was removed, and the cells were harvested by treatment with trypsin. The suspension was pelleted by centrifugation for 5 min at 800×g and resuspended in 0.6 mL PBS buffer. The suspension was sonicated to lyse the cells. For further analysis, protein concentrations were determined using the $D_c$ Protein Assay Kit (Bio-Rad). The proteome was used immediately, or stored at −80° C. Prior to use, the concentration of the final supernatants was adjusted to 1.5 mg/ml.

For labeling with the FP-PEG-TMR probe, the proteomes were analyzed as follows: To an aliquot (0.050 mL) of the selected proteome was added a solution of FP-PEG-TMR (100 μM in DMSO) to a final concentration of 2 μM. The mixture was allowed to stand at room temperature for 1 hour, quenched using an equal volume of loading buffer (reducing). A sample (0.025 mL; 0.018 mg protein) of the solution was removed and separated on a 10% SDS gel. The gels were then imaged on a Hitachi FMbio Flatbed Fluorescence Scanner, with excitation provided by the 532 nm line of a 20 mW YAG laser, and detection at 580 nm using a bandpass filter assembly provided by the manufacturer. To assess the quality of the electropherograms, samples were also reacted with a biotin analog of the fluorescer and analyzed using published procedures (see Liu, Y., Patricelli, M P, & Cravatt, B F (1999) PNAS 96 (26)14694–14699). Background signal was analyzed in both cases using a boiled control sample. Surprisingly, the fluorescent TMR-labeled probe provided equal or increased sensitivity in comparison to the biotin-labeled probe. Additionally, the use of a PEG linker in these molecules proved advantageous in comparison to alkyl linkers.

In the next study a multiplexed analysis of the same proteomes employed above was performed. A sample containing purified fatty acid amide hydrolase (FAAH) labeled with FP-PEG-TMR (10 or 100 ng, as noted) was mixed with rat testis cytosol labeled with FP-PEG-Fluorescein (18 ug). The samples were electrophoresed as described above. The results showed the utility of the fluorescent multiplexed analysis to obtain information regarding the functional status of FAAH in the rat testis proteome.

It is evident from the above results that many advantages accrue from the methodology of the subject invention. There is no need for a blotting or development step. Fluorescence measurements are accomplished more quickly and continuously with direct measurement using a commercial scanner attached to an electrophoresis rig. The fluorescent tags allow for subsequent manipulation of the proteomic conjugates, including proteolysis, to facilitate both detection and identification. By using more than one probe in the same reaction mixture allows for more robust detection, including internal controls, direct comparison of cross-reactivity between probes, suggesting analogous active sites for different proteins, and assurance of identical conditions during the reaction of the probes, the subsequent workup and analysis. Direct comparisons between native and inactivated protein conjugates can be made where the electrophoretic bands are superimposed or appear as proximate pairs. Proteins that do not react do not provide a fluorescent signal, so that one can obtain results with no or minor purification or processing of the reaction mixture.

Example 3

Synthesis of 5'-Amido ATP-Based Probes

5'-(Boc)-amino-2'(3')-(2-aminoethylcarbamoyl)adenosine (15)

To 5'-amino adenosine (20 mg, 0.075 mmol) dissolved in DMF (1 ml) was added di-t-butyl dicarbonate (14 mg, 0.075 mmol) and the resulting clear solution stirred at room temperature. After 30 minutes carbonyldiimidazole (24 mg, 0.15 mmol, 2 eq.) was added and the resulting clear solution stirred at room temperature for 3 hours. The reaction was quenched with methanol (0.5 ml) and volatiles removed under high vacuum leaving a white solid. The solid was dissolved in DMF (1 ml), and ethylene diamine (50 µl, 55.6 mg, 0.75 mmol, 10 eq.) added to yield a clear solution that was stirred at room temperature. After 10-minutes, LC-MS confirmed that the reaction was complete (isomers inseparable by LC—one peak) and indicated that 15 (24 mg, 0.053 mmol, 71%) had been formed in purity suitable for the next step. An analytical sample was prepared by preparative HPLC and was analyzed by $^1$H-NMR. It was a 65/35 mixture of two isomers having the characteristic nucleoside $^1$H chemical shifts: glycosidic CH 5.90 (d, 1H) and 6.12 (d, 1); imidazole CH 8.59 (s, 1H) and 8.63 (s, 1H); pyridazine CH 8.39 (s, 1H) and 8.41 (s, 1H); BOC t-butyl CH$_3$ 1.36 (s, 9H) and 1.38 (s, 9H) ppm. It had mass spectrum: [MH$^+$]=453.2 amu (calculated for $C_{18}H_{28}N_8O_6$ 452.48 amu).

5'-Amino-2'(3')-(2-TAMRA-amidoethylcarbamoyl)adenosine (16)

At room temperature, 5'-(Boc)-amino-2'(3')-(2-aminoethylcarbamoyl)adenosine 15 (8 mg, 0.018 mmol) was dissolved in DMF (0.5 ml) followed by addition of TAMRA-SE (10 mg, 0.019 mmol, 1.05 eq.) dissolved in DMF (1 ml). After 30 minutes (2 isomers now separable by LC) volatiles were removed under high-vacuum leaving a red residue. The residue was dissolved in TFA (1 ml) for 1-minute, then concentrated under high vacuum. LC-MS shows completion of reaction and again two isomers were observed. Preparative HPLC (the most abundant and easily separated of the two isomers was harvested [this isomer had the longest retention time of the two on a C8 reverse phase column]) yielded 16 as a TFA salt (8.5 mg, 0.010 mmol, 54%). It had mass spectrum: [MH$^+$]=765.3 amu (calculated for $C_{38}H_{40}N_{10}O_8$ 764.80 amu).

5'-Amino-2'(3')-(2-BODIPY-FL-amidoethylcarbamoyl)adenosine (17)

The BODIPY-FL analogue 17 was prepared in exactly the same manner as 16 except that BODIPY-FL succinimidyl ester was used in place of TAMRA succinimidyl ester. The isomeric products were separated similarly on HPLC with the most abundant isomer taken on to the next step. It had mass spectrum: [MH$^+$]=627.3 amu (calculated for $C_{27}H_{33}BF_2N_{10}O_5$ 626.43 amu).

5'-Amino-2'(3')-(2-rhodamine green-amidoethylcarbamoyl)adenosine (18)

The rhodamine green analogue 18 was prepared in exactly the same manner as 16 except that rhodamine green succinimidyl ester was used in place of TAMRA succinimidyl ester. The isomeric products were separated on HPLC with the most abundant being taken on to the next step. It had mass spectrum: [MH$^+$]=709.3 amu (calculated for $C_{34}H_{32}N_{10}O_8$ 708.69 amu).

5'-FSB-amido-2'(3')-(2-TAMRA-amidoethylcarbamoyl)adenosine (19)

To 5'-Amino-2'(3')-(2-TAMRA-amidoethylcarbamoyl)adenosine (16) (2 mg, 2.62 µmol, [TFA salt]) dissolved in DMF (1 ml) was added 4-fluorosulfonylbenzoylchloride (3 mg, 40.4 µmol, 20 eq.). Triethylamine was then added portion wise (3×5 µl) over 15 minutes at room temperature. LC-MS showed a mono-adduct as the major product among several by-products. The compound was isolated by preparative HPLC to yield 19 (1.9 mg, 1.78 µmol, 70%). It had mass spectrum: [MH$^+$]=951.3 amu (calculated for $C_{45}H_{43}FN_{10}O_{11}S$ 950.96 amu).

5'-(4"-Vinylsulfonylbenzoyl)amido-2'(3')-(2-TAMRA amidoethylcarbamoyl)adenosine (20)

The 5'-vinylsulfonylbenzoyl probe 20 was prepared in the same manner as 19, however, succinimidyl-(4-vinylsulfonyl)benzoate was used in place of 4-fluorosulfonyl-benzoylchloride. Preparative HPLC yielded 20 in 82% yield. It had mass spectrum: [MH$^+$]=959.3 amu (calculated for $C_{47}H_{46}N_{10}O_{11}S$ 959.03 amu).

5'-Acrylamido-2'(3')-(2-TAMRA-amidoethylcarbamoyl)adenosine (21)

The 5'-acrylamido probe 21 was prepared in the same manner as 19 however, acryloyl chloride was used in place of 4-fluorosulfonylbenzoylchloride. Preparative HPLC yielded 21 in 75% yield. It had mass spectrum: [MH$^+$]=819.3 amu (calculated for $C_{41}H_{42}N_{10}O_9$ 818.84 amu).

5'-α-Chloroacetamido-2'(3')-(2-TAMRA-amidoethylcarbamoyl)adenosine (22)

The 5'-α-chloroacetamido probe 22 was prepared in the same manner as 19, however, chloroacetyl chloride was used in place of 4-fluorosulfonylbenzoylchloride. Preparative HPLC yielded 22 in 92% yield. It had mass spectrum: [MH$^+$]=841.3 amu (calculated for $C_{40}H_{41}FN_{10}O_9$ 841.28 amu).

5'-FSB-amido-2'(3')-(2-BODIPY-FL-amidoethylcarbamoyl)adenosine (23)

The BODIPY-FL FSBA probe analogue 23 was prepared from 17 using similar conditions to that of 19 with similar HPLC purification to provide 23 in 69% yield. It had mass spectrum: [MH$^+$]=813.3 amu (calculated for C$_{34}$H$_{36}$BF$_3$N$_{10}$O$_8$S 812.59 amu).

5'-FSB-amido-2'(3')-(2-rhodamine green-amidoethylcarbamoyl)adenosine (24)

The rhodamine green FSBA probe analogue 24 was prepared from 18 using similar conditions to that of 19 with similar HPLC purification to provide 24 in 79% yield. It had mass spectrum: [MH$^+$]=895.2 amu (calculated for C$_{41}$H$_{35}$FN$_{10}$O$_{11}$S 894.85 amu).

Example 4

Synthesis of 5'-Ester ATP-Based Probes

5'-Monomethoxytrityl-2'(3)-(2-aminoethylcarbamoyl)adenosine (25)

5'-Monomethoxyltrityl adenosine (200 mg, 0.37 mmol) was dissolved in DMF (3 ml) and to the resulting clear solution was added carbonyl diimidazole (120 mg, 0.74 mmol, 2 eq.). After 2 hours the reaction was quenched with methanol (0.5 ml). The volatiles were removed under vacuum to leave a clear syrup which was then dissolved in DMF (1 ml) followed by ethylene diamine (80 µl, 1.20 mmol, ca. 4 eq.). LC-MS indicated that the reaction was complete within minutes and the volatiles were removed under vacuum to yield 25 as a viscous clear syrup pure enough for the next step. An analytical sample was purified by preparative HPLC. It was analyzed by $^1$H-NMR and was shown to be a 65/35 mixture of isomers (and an unavoidable small amount of detritylated material due to the presence of TFA in the HPLC buffers). The isomers had characteristic nucleoside $^1$H chemical shifts: glycosidic CH 5.92 (d, 1H) and 6.09 (d, 1H); imidazole CH 8.23 (s, 1H) and 8.26 (s, 1H); pyridazine CH 8.07 (s, 1H) and 8.09 (s, 1H); methoxy CH$_3$ 3.72 (s, 3H) and 3.72 (s, 3H) ppm. It had mass spectrum: [MH$^+$]=626.3 amu (calculated for C$_{33}$H$_{35}$N$_7$O$_6$ 625.68 amu).

5'-Hydroxy-2'(3')-(2-T AMRA-amidoethylcarbamoyl)adenosine (26)

5'-Monomethoxytrityl-2'(3')-(2-aminoethylcarbamoyl) adenosine 25 (30 mg, 48.0 µmol) was dissolved in DMF (300 µl) and TAMRA succinimidyl ester (25 mg, 48.0 µmol) dissolved in DMF solution (250 µl) added. The resulting red solution was then allowed to stir at room temperature for 30 minutes. LC-MS confirmed completion of reaction. Removal of the volatiles provided a red residue that was then momentarily exposed to neat TFA (orange solution). Removal of the volatiles and purification by preparative HPLC yielded 26 as a clear residue. LC-MS confirmed the desired compound had been made. It had mass spectrum: [MH$^+$]=766.3 amu (calculated for C$_{38}$H$_{39}$N$_9$O$_9$ 765.78 amu).

5'-α-Chloroacetyl-2'(3')-(2-TAMRA-amidoethylcarbamoyl)adenosine (27).

5'-Hydroxy-2'(3')-(2-TAMRA-amidoethylcarbamoyl)adenosine 26 (2.0 mg, 2.6 µmol) was dissolved in DMF (250 µl) before chloroacetyl chloride (3 µl, 38 µmol) was added. The resulting red solution was stirred at room temperature for 1 hour. The desired compound 27 (1.4 mg, 1.7 µmol, 65%) was isolated by preparative HPLC. It had mass spectrum: [MH$^+$]=842.3 amu (calculated for C$_{40}$H$_{40}$ClN$_9$O$_{10}$ 842.26 amu).

5'-FSB-acetyl-2'(3')-(2-TAMRA-amidoethylcarbamoyl) adenosine (28)

5'-Hydroxy-2'(3')-(2-TAMRA-amidoethylcarbamoyl)adenosine 26 (2.0 mg, 2.6 µmol) was dissolved in DMF (250 µl) before fluorosulfonylbenzoyl chloride hydrochloride (15 mg, 30.6 µmol) was added in 3 portions (over 45 minutes). Each addition of the flurosulfonylbenzoyl chloride was followed by addition of 5 µl of triethylamine. LC-MS indicated that after 1 hour, most of the starting material was consumed and preparative HPLC yielded 28. An analytical sample was submitted for HRMS and showed: [MH$^+$]=952.2695 amu with an error of ±3.7 ppm (calculated for C$_{45}$H$_{42}$FN$_9$O$_{12}$S: 952.273 amu).

Example 5

Gel Analysis Platform

Gel plates made of low fluorescence borosilicate glass with dimensions of 20 cm×28 cm were used to cast gels 0.4 mm thick polyacrylamide gels. The plates use a microtrough system (CBS Scientific, Del Mar Calif.) which allows for vertical loading of samples into ultrathin gels using standard pipette tips. Additionally, the microtrough system allows for very close spacing of adjacent wells (as close as 2.25 mm). Using tetramethylrhodamine-based fABPs, acceptable signals were obtained from tissue samples with as little as 1 µg of protein in 3 µL, with an absolute detection limit for a fluorescently labeled protein in the range of 0.01–0.05 fmol ($1-5\times10^{-17}$ moles). Such sample requirements are approximately 10 fold lower than those typically observed for standard SDS-PAGE apparatus. The gels were run for 1 hour at 1000V with aluminum heat dispersion plates. The time required for running these gels is approximately 4 fold less than comparable sized, 1.5 mm thick SDS-PAGE gels.

Commercial laser scanners use laser focusing and confocal collection optics to allow for scanning of a defined section, or slice, of any particular sample. In addition, depth may be set so that the laser and collection optics focus into the gel, through the gel running plates. Because 0.4 mm thick gels are extremely difficult to handle, the ability to scan the gel without having to remove it from the glass plates is particularly advantageous. Using a Hitachi FMBIO® IIe imaging system, the confocal slice thickness was 0.4 mm. The high resolution of these scanners (83 µM pixel size) allows for very narrow electrophoresis lanes to be run without a loss in sensitivity. For example, a 1 mm wide lane would represent approximately 12 datapoints in the horizontal direction.

Example 6

Selection of Anti-Fluorophore Antibodies

Monoclonal antibodies were generated against tetramethyl rhodamine (TMR) using standard procedures. Briefly, TMR-succinimidyl ester was reacted with keyhole limpet hemocyanin to generate a hapten for immunization of mice. Mice were immunized and later screened using an ELISA assay to measure the production of antibodies that bind TMR. In the ELISA screens, TMR linked to bovine serum albumin was used. Speenocytes from positive mice were then fused to lymphoma cells to generate hybridoma lines. The hybridoma lines were then screened by ELISA.

Following the initial screening of the hybridoma lines using standard conditions, two specific screens were used. First, two positional isomers of tetramethylrhodamine were individually screened to find antibodies that did not differentiate between the 5 and 6-carboxy TMR isomers. This was done to allow flexibility in the chemical nature of the pendant phenyl ring of TMR for fABP design. A second screen was performed at pH 2.5 to identify antibodies that were functional at this extreme pH. Several thousand antibodies were screened in these experiments. Many (100s) exhibited very little discrimination between the two TMR isomers. Only one showed robust binding at pH 2.5. Ten antibodies were selected based on the above criteria as well as their overall strong ELISA signals.

These ten antibodies were then produced using mouse ascites and the antibodies were purified and individually screened for their TMR binding affinity and function in an FABP labeled protein enrichment assay. Purified antibodies were coupled to Affi-gel Hz beads (Bio-Rad) according to manufacturers recommendations at a density of 4–5 mg/mL of beads. These beads were then used to enrich fABP labeled proteins according to the attached protocol. Of these ten antibodies, two were found to be very poor binders of TMR and were not analyzed for protein capture. One antibody was produced very poorly in the ascited fluid and sufficient quantities could not be obtained for analysis. Of the seven other antibodies, a range of performance was observed. The antibody identified as being capable of binding TMR at pH 2.5 was the best performing antibody in these screens, binding roughly 2–5 times as much protein as the second best antibody. This antibody was selected for subsequent fABP-labeled protein capture experiments.

Example 7

Antibody Capture of fABP-Labeled Proteins

1. Sample was labeled with a TAMRA- or TMR-labeled probe;
2. 80 mg urea was added per 100 uL of sample;
3. DTT was added to 10 mM from a fresh 1M stock;
4. The resulting reaction mixture was heated to 65° C. for 20 min;
5. The heated reaction mixture was cooled to room temperature, and Iodoacetamide was added to 40 mM from a fresh 1M stock;
6. The resulting mixture was incubated at 37° C. for 45 minutes in the dark, then added to a Pharmacia PD-10 or Bio-Rad 1-DG column (preequilibrated with 2M urea, 20 mM ammonium bicarbonate). Eluted protein (as determined by monitoring absorbance at 280 nm to find the protein peak) was collected;
9. 1/10 volume of 10% SDS was added to the pooled fractions, and the resulting mixture was heated to 65° C. for 5 minutes;
10. The resulting mixture was mixed with 1 volume of 2×Binding Buffer (2% Triton X-100, 1% Tergitol NP40 type, 300 mM NaCl, 2 mM EDTA, 20 mM Tris pH 7.4) and antibody beads (from 30–200 uL of 50% bead slurry to yield 15–100 uL of beads) were added;
12. The bead mixture was rocked at room temperature;
13. Beads were removed by spinning in a picofuge and removing the supernatant. The beads were washed at least three times with 1 mL of 1×binding buffer+0.2% SDS, then at least twice with 0.5 mL of 50 mM tris, 100 mM;
16. Captured proteins were then eluted from the beads using 1 bed volume of 1×non-reducing loading/elution buffer (50 mM Tris pH 7.5, 10% glycerol, 5% SDS, 150 mM NaCl, bromophenol blue (5 mg/50 mL)). The beads were incubated in this buffer at least 10 minutes at 65° C. for 10 minutes;
17. The resulting solution (beads and buffer liquid) were loaded onto a micro spin column and spun at 5000 rpm for 3 minutes in a microcentrifuge;
18. DTT was added to a concentration of 10 mM, and the mixture boiled briefly before loading onto a polyacrylamide gel.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

While the invention has been described in detail with reference to certain preferred embodiments thereof, it will be understood that modifications and variations are within the spirit and scope of that which is described and claimed.

What is claimed is:

1. A method for analyzing a complex protein mixture, said method comprising:

labeling one or more active target proteins present in said complex protein mixture by combining at least one probe specific for one or more active target proteins with said complex protein mixture under conditions whereby said probe(s) covalently react with said active target proteins;

isolating one or more of said labeled active target proteins by binding to a receptor bound to a solid phase, wherein said receptor binds the probe labeling said active target proteins, removing unbound proteins, and releasing bound labeled active target proteins from said receptor; and detecting a signal from one or more labeled active target proteins present in said complex protein mixture following said isolating, wherein said signal is detected by separating one or more of said labeled active target proteins and generating a fluorescent signal from one or more of said labeled active target proteins during or following said separation;

wherein said probe has the structure:

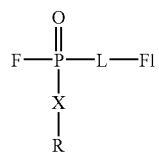

wherein:
X is —CH$_2$—, —O—, or —S—;
R is —H or a chain of from 1–20 carbon atoms and from 0 to 5 heteroatoms, which chain is straight or branched alkyl, alkenyl, or alkynyl optionally comprising one or more aromatic, alicyclic, heteroaromatic, or heterocyclic groups;

L is a linker moiety comprising from about 2 to 20 carbon atoms and having from 0 to 10 heteroatoms, wherein L is aliphatic, alicyclic, aromatic or heterocyclic; and Fl is a fluorescent moiety and F is fluorine.

2. A method according to claim 1, wherein said separation comprises applying all or a portion of said labeled active target proteins to an electrophoretic medium for separation of said labeled active target proteins; and generating a fluorescent signal from one or more separated active target proteins, whereby said fluorescent signal indicates the presence of an active target protein in said complex protein mixture reactive with said at least one probe.

3. A method according to claim 2, wherein said separation comprises SDS-PAGE.

4. A method according to claim 2, wherein said separation comprises capillary electrophoresis.

5. A method according to claim 2, further comprising:
isolating at least one fluorescent band from said electrophoretic medium; and
identifying one or more labeled active target proteins present in said fluorescent band.

6. A method according to claim 1, wherein said fluorescent moiety exhibits a peak absorbance wavelength in the visible spectrum, and exhibits a peak emission wavelength in the visible spectrum.

7. A method according to claim 1, wherein said fluorescent moiety is a rhodamine.

8. A method according to claim 7, wherein said rhodamine is 5-carboxytetramethylrhodamine or 6-carboxytetramethylrhodamine.

9. A method according to claim 1, wherein said complex protein mixture is a proteome.

10. A method according to claim 1, wherein said receptor comprises an antibody which binds said probe.

11. A method for analyzing a complex protein mixture, said method comprising:

labeling one or more active target proteins present in said complex protein mixture by combining at least one probe specific for one or more active target proteins with said complex protein mixture under conditions whereby said probe(s) covalently react with said active target proteins;

isolating one or more of said labeled active target proteins by binding to a receptor bound to a solid phase, wherein said receptor binds the probe labeling said active target proteins, removing unbound proteins, and releasing bound labeled active target proteins from said receptor; and detecting a signal from one or more labeled active target proteins present in said complex protein mixture following said isolating, wherein said signal is detected by separating one or more of said labeled active target proteins and generating a fluorescent signal from one or more of said labeled active target proteins during or following said separation;

wherein said probe has the structure:

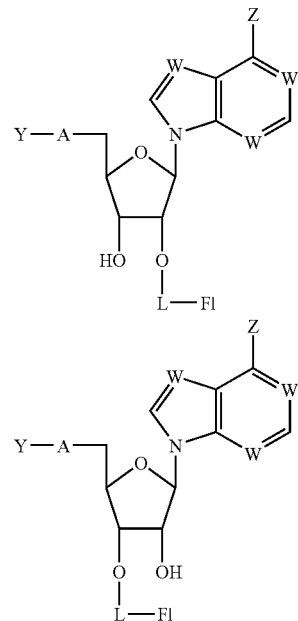

wherein:
each W is independently carbon or nitrogen;
Z is hydrogen or amino;
Y is a functional group capable of reacting with at least one of thiol, hydroxyl or amino joined through A to the 5' carbon of the ribose, where the functional group may be directly bonded to A or through a link, the functional group being one or more moieties comprising halogen, O, S, N, P, or C, selected from the group consisting of fluorosulfonyl, fluorophosphonyl ester, halogen, epoxide, ethylene α to an activating group, and halogen β to an activating group;
A is NR, O, S or $CH_2$, wherein R is H or alkyl of from 1 to 6 carbon atoms; and
Fl is a fluorescent moiety joined to the oxygen of the 2' or 3' position of the ribose through a linker moiety L of at least 2 atoms, said linker moiety L comprising carbon, oxygen, nitrogen or sulfur.

12. A method according to claim 11, wherein said separation comprises applying all or a portion of said labeled active target proteins to an electrophoretic medium for separation of said labeled active target proteins; and generating a fluorescent signal from one or more separated active target proteins, whereby said fluorescent signal indicates the presence of an active target protein in said complex protein mixture reactive with said at least one probe.

13. A method according to claim 12, wherein said separation comprises SDS-PAGE.

14. A method according to claim 12, wherein said separation comprises capillary electrophoresis.

15. A method according to claim 11, wherein said functional group is selected from the group consisting of an alkylating functionality, an acylating functionality, a ketone functionality, an epoxide functionality, an aldehyde functionality, a sulphonyl functionality and a phosphoryl functionality.

16. A method according to claim 12, further comprising;
isolating at least one fluorescent band from said electrophoretic medium; and
identifying one or more labeled active target proteins present in said fluorescent band.

17. A method according to claim 11, wherein said fluorescent moiety exhibits a peak absorbance wavelength in the visible spectrum, and exhibits a peak emission wavelength in the visible spectrum.

18. A method according to claim 11, wherein said fluorescent moiety is a rhodamine.

19. A method according to claim 18, wherein said rhodamine is 5-carboxytetramethylrhodamine or 6-carboxytetramethylrhodamine.

20. A method according to claim 11, wherein said complex protein mixture is a proteome.

21. A method according to claim 11, wherein said receptor comprises an antibody which binds said probe.

* * * * *